(12) United States Patent
Njar et al.

(10) Patent No.: US 8,785,423 B2
(45) Date of Patent: Jul. 22, 2014

(54) COMPOSITIONS AND METHODS OF INDUCING ENDOPLASMIC RETICULUM STRESS RESPONSE FOR THE TREATMENT OF CELL PROLIFERATIVE DISEASES

(75) Inventors: Vincent Njar, Landsdale, PA (US); Angela Brodie, Fulton, MD (US); Robert Bruno, Columbia, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 7 days.

(21) Appl. No.: 12/937,900

(22) PCT Filed: Apr. 14, 2009

(86) PCT No.: PCT/US2009/040448
§ 371 (c)(1),
(2), (4) Date: Feb. 17, 2011

(87) PCT Pub. No.: WO2009/129208
PCT Pub. Date: Oct. 22, 2009

(65) Prior Publication Data
US 2011/0160170 A1  Jun. 30, 2011

Related U.S. Application Data

(60) Provisional application No. 61/044,621, filed on Apr. 14, 2008.

(51) Int. Cl.
*A01N 45/00* (2006.01)
*A61K 31/56* (2006.01)
*A61K 31/58* (2006.01)
*A61K 45/06* (2006.01)
*A61K 33/24* (2006.01)

(52) U.S. Cl.
CPC ................ *A61K 31/58* (2013.01); *A61K 45/06* (2013.01); *A61K 33/24* (2013.01)
USPC ............................ 514/171; 514/176; 514/182

(58) Field of Classification Search
None
See application file for complete search history.

(56) References Cited

U.S. PATENT DOCUMENTS

| 4,000,125 | A | 12/1976 | Casagrande et al. |
|---|---|---|---|
| 5,601,981 | A | 2/1997 | Malins |
| 5,604,213 | A | 2/1997 | Barrie et al. |
| 5,994,334 | A | 11/1999 | Brodie et al. |
| 5,994,335 | A | 11/1999 | Brodie et al. |
| 6,133,280 | A | 10/2000 | Brodie et al. |
| 6,200,965 | B1 | 3/2001 | Brodie et al. |
| 6,368,598 | B1 * | 4/2002 | D'Amico et al. .......... 424/181.1 |
| 6,444,683 | B2 | 9/2002 | Brodie et al. |
| 7,875,599 | B2 | 1/2011 | Brodie |
| 2001/0001099 | A1 | 5/2001 | Brodie et al. |
| 2003/0054053 | A1 | 3/2003 | Young et al. |
| 2008/0280864 | A1 | 11/2008 | Brodie |
| 2010/0047338 | A1 | 2/2010 | Brodie et al. |
| 2010/0048524 | A1 | 2/2010 | Brodie et al. |
| 2010/0048912 | A1 | 2/2010 | Brodie et al. |
| 2010/0048913 | A1 | 2/2010 | Brodie et al. |
| 2010/0048914 | A1 | 2/2010 | Brodie et al. |
| 2010/0137269 | A1 | 6/2010 | Brodie et al. |
| 2011/0034428 | A1 | 2/2011 | Morrison et al. |
| 2011/0105445 | A1 | 5/2011 | Njar et al. |
| 2011/0118219 | A1 | 5/2011 | Njar et al. |
| 2011/0312916 | A1 | 12/2011 | Casebier |
| 2011/0312924 | A1 | 12/2011 | Casebier |
| 2011/0319369 | A1 | 12/2011 | Casebier et al. |

FOREIGN PATENT DOCUMENTS

| WO | WO 2005/014023 A1 | 2/2005 |
|---|---|---|
| WO | WO 2006/093993 * | 9/2006 |

OTHER PUBLICATIONS

Humez et al. Role of endoplasmic reticulum calcium content in prostate cancer cell growth regulation by IGF and TNFalpha. Journal of Cellular Physiology, 201: 201-213. 2004.*
U.S. Appl. No. 13/508,726, filed May 8, 2012, Chappel et al.
Barrie, et al. Pharmacology of novel steroidal inhibitors of cytochrome P450(17) alpha (17 alpha-hydroxylase/C17-20 lyase). J Steroid Biochem Mol Biol. Sep. 1994;50(5-6):267-73.
Bruchovsky, et al. The conversion of testosterone to 5-alpha-androstan-17-beta-ol-3-one by rat prostate in vivo and in vitro. J Biol Chem. Apr. 25, 1968;243(8):2012-21.
Bruno, et al. Targeting cytochrome P450 enzymes: a new approach in anti-cancer drug development. Bioorg Med Chem. Aug. 1, 2007;15(15):5047-60.
Chen, et al. Molecular determinants of resistance to antiandrogen therapy. Nat Med. Jan. 2004;10(1):33-9.
Chengjie, et al. Synthesis of pharmacological activity of some 17-[(2'-substituted)-4'-pyramidyl] androstene derivatives as inhibitors of human 17alpha-hydroxylase/C17,20-layse. J. Chinese Pharm. Sci. 2001; 10(1):3-8.
Choshi, et al. Total synthesis of grossularines-1 and -2. J. Org. Chem. 1995; 60:5899-5904.
Christenen, et al. Thapsigargin analogues for targeting programmed death of androgen-independent prostate cancer cells. Bioorg Med Chem. Jul. 1999;7(7):1273-80.
Clement, et al. Three dimensional pharmacophore modeling of human CYP17 inhibitors. Potential agents for prostate cancer therapy. J Med Chem. Jun. 5, 2003;46(12):2345-51.

(Continued)

*Primary Examiner* — Anna Pagonakis
(74) *Attorney, Agent, or Firm* — Wilson Sonsini Goodrich & Rosati

(57) ABSTRACT

The present invention provides methods of inducing cell cycle arrest and/or cell growth inhibition, with the methods comprising administering to the cells an effective dose of the compounds of the present invention.

8 Claims, 14 Drawing Sheets

(56) References Cited

OTHER PUBLICATIONS

Crawford, et al. A controlled trial of leuprolide with and without flutamide in prostatic carcinoma. New Eng J Med. 1989; 321:419-424.

Crawford, et al. Treatment of newly diagnosed stage D2 prostate cancer with leuprolide and flutamide or leuprolide alone, phase III: prognostic significance of minimal disease. J. Urol. 1992; 147:417A.

Denis. Role of maximal androgen bloackade in advanced prostate cancer. The Prostate Supplement. 1994; 5:17-22.

Denmeade, et al. A history of prostate cancer treatment. Nat Rev Cancer. 2002; 2(5):389-96.

Evans, et al. methods for drug discovery: development of potent, selective, orally effective cholecystokinin antagonists. J Med Chem 1988; 31(12):2235-46.

Grigoryev, et al. Cytochrome P450c17-expressing *Escherichia coli* as a first-step screening system for 17alpha-hydroxylase-C17,20-lyase inhibitors. Anal Biochem. Feb. 15, 1999;267(2):319-30.

Grigoryev, et al. Effects of new 17alpha-hydroxylase/C(17,20)-lyase inhibitors on LNCaP prostate cancer cell growth in vitro and in vivo. Br J Cancer. Oct. 1999;81(4):622-30.

Haidar, et al. Effects of novel 17alpha-hydroxylase/C17, 20-lyase (P450 17, CYP 17) inhibitors on androgen biosynthesis in vitro and in vivo. J Steroid Biochem Mol Biol. Apr. 2003;84(5):555-62.

Haidar, et al. Novel steroidal pyrimidyl inhibitors of P450 17 (17 alpha-hydroxylase/C17-20-lyase). Arch Pharm (Weinheim). Dec. 2001;334(12):373-4.

Hall. Cytochrome P-450 C21scc: one enzyme with two actions: hydroxylase and lyase. J Steroid Biochem Mol Biol. 1991;40(4-6):527-32.

Handratta, et al. Novel C-17-heteroaryl steroidal CYP17 inhibitors/antiandrogens: synthesis, in vitro biological activity, pharmacokinetics, and antitumor activity in the LAPC4 human prostate cancer xenograft model. J Med Chem. Apr. 21, 2005;48(8):2972-84.

Handratta, et al. Potent CYP17 inhibitors: improved syntheses, pharmacokinetics and anti-tumor activity in the LNCaP human prostate cancer model. J Steroid Biochem Mol Biol. Oct. 2004;92(3):155-65.

Hartmann, et al. Synthesis and evaluation of novel steroidal oxime inhibitors of P450 17 (17 alpha-hydroxylase/C17-20-lyase) and 5 alpha-reductase types 1 and 2. J Med Chem. Nov. 2, 2000;43(22):4266-77.

Huggins, et al. Studies in prostate cancer: The effects of castration on advanced carcinoma of the prostate gland. Arch Surg. 1941; 43(2):209-223.

Humber, et al. Synthesis and biological activity of some cardiotonic compounds related to digitoxigenin. Steroids. Aug. 1983;42(2):189-202.

International search report and written opinion dated Nov. 30, 2009 for PCT/US2010/040448.

International search report dated Oct. 7, 2009 for PCT/US2009/036891.

Jarman, et al. The 16,17-double bond is needed for irreversible inhibition of human cytochrome p45017alpha by abiraterone (17-(3-pyridyl)androsta-5, 16-dien-3beta-ol) and related steroidal inhibitors. J Med Chem. Dec. 31, 1998;41(27):5375-81.

Jefcoate. Measurement of substrate and inhibitor binding to microsomal cytochrome P-450 by optical-difference spectroscopy. Methods Enzymol. 1978;52:258-79.

Jemal, et al. Cancer statistics, 2004. CA cancer J. Clin. 2004; 54(1):8-29.

Kadar, et al. Technical and safety aspects of blood and marrow transplantation using G-CSF mobilized family donors. Transfus Sci. Dec. 1996;17(4):611-8.

Kim, et al. Synergism of cytoplasmic kinases in IL6-induced ligand-independent activation of androgen receptor in prostate cancer cells. Oncogene. Mar. 11, 2004;23(10):1838-44.

Klein, et al. Progression of metastatic human prostate cancer to androgen independence in immunodeficient SCID mice. Nat Med. Apr. 1997;3(4):402-8.

Ling, et al. 17-Imidazolyl, pyrazolyl, and isoxazolyl androstene derivatives. Novel steroidal inhibitors of human cytochrome C17,20-lyase (P450(17 alpha). J Med Chem. Sep. 26, 1997;40(20):3297-304.

Long, et al. Antiandrogenic effects of novel androgen synthesis inhibitors on hormone-dependent prostate cancer. Cancer Res. Dec. 1, 2000;60(23):6630-40.

Matsunaga, et al. C17,20-lyase inhibitors I. Structure-based de novo design and SAR study of C17,20-lyase inhibitors. Bioorg Med Chem. May 1, 2004;12(9):2251-73.

Matsunaga, et al. Synthetic studies on (1S)-1-(6,7-dimethoxy-2-naphthyl)-1-(1H-imidazol-4-yl)-2-methylpropan-1-ol as a selective C17,20-lyase inhibitor. Tetrahedron: Asymmetry. 2004; 15:2021-2028.

Matsunaga, et al. C(17,20)-lyase inhibitors. Part 2: design, synthesis and structureactivity relationships of (2-naphthylmethyl)-1H-imidazoles as novel C(17,20)-lyase inhibitors. Bioorg Med Chem. Aug. 15, 2004;12(16):4313-36.

McConnell. Physiologic basis of endocrine therapy for prostatic cancer. Urol Clin North Am. Feb. 1991;18(1):1-13.

Mohler, et al. The androgen axis in recurrent prostate cancer. Clin Cancer Res. Jan. 15, 2004;10(2):440-8.

Moreira, et al. Synthesis and evaluation of novel 17-indazole androstene derivatives designed as CYP17 inhibitors. Steroids. Dec. 2007;72(14):939-48.

Muscato, et al. Optimal dosing of ketoconazole (KETO) and hydrocortisone (HC) leads to long responses in hormone refractory prostate cancer. Proc ASCO. 1994; 229:701.

Nicolaou, et al. Natural Product-like Combinatorial Libraries Based on Privileged Structures. 1. General Principles and Solid-Phase Synthesis of Benzopyrans. J. Am. Chem. Soc. 2000; 122(41):9939-9953.

Njar, et al. Inhibitors of 17alpha-hydroxylase/17,20-lyase (CYP17): potential agents for the treatment of prostate cancer. Curr Pharm Des. Mar. 1999;5(3):163-80.

Njar, et al. Novel 17-azolyl steroids, potent inhibitors of human cytochrome 17 alpha-hydroxylase-C17,20-lyase (P450(17) alpha): potential agents for the treatment of prostate cancer. J Med Chem. Mar. 12, 1998;41(6):902-12.

Njar, et al. Nucleophilic vinylic 'Addition-Elimination' Substitution Reaction of 3B-Acetoxy-17-Chloro-16-Formylandrosta-5,16-Diene: A Novel and General Route to 17-Substituted Steroids Bioorganic and Medical Chemistry Letters 1996; 6(22):2777-27820.

Nnane, et al. Effects of novel 17-azoly1 compounds on androgen synthesis in vitro and in vivo. J Steroid Biochem Mol Biol. Dec. 15, 1999;71(3-4):145-52.

O'Donnell, et al. Hormonal impact of the 17alpha-hydroxylase/C(17,20)-lyase inhibitor abiraterone acetate (CB7630) in patients with prostate cancer. Br J Cancer. Jun. 14, 2004;90(12):2317-25.

Office Action dated Jan. 31, 2011 for U.S. Appl. No. 12/577,094.

Office action dated Mar. 7, 2012 for JP Application No. 2007-558143 (in English).

Office Action dated Mar. 12, 2010 for U.S. Appl. No. 11/817,550.

Office action dated Mar. 23, 2012 for EP Application No. 10150763.0.

Office Action dated Apr. 4, 2012 for U.S. Appl. No. 12/577,090.

Office Action dated May 5, 2010 for U.S. Appl. No. 12/577,091.

Office Action dated May 7, 2010 for U.S. Appl. No. 12/577,092.

Office Action dated May 23, 2011 for U.S. Appl. No. 12/577,094.

Office Action dated May 25, 2010 for U.S. Appl. No. 12/577,096.

Office Action dated Jun. 1, 2010 for U.S. Appl. No. 12/577,090.

Office Action dated Jun. 1, 2011 for U.S. Appl. No. 12/623,257.

Office Action dated Jun. 2, 2010 for U.S. Appl. No. 11/817,550.

Office Action dated Sep. 8, 2011 for U.S. Appl. No. 12/577,096.

Office Action dated Sep. 9, 2011 for U.S. Appl. No. 12/577,090.

Office Action dated Oct. 17, 2012 for U.S. Appl. No. 12/577,090.

Office Action dated Oct. 20, 2010 for U.S. Appl. No. 12/623,257.

Office Action dated Oct. 28, 2010 for U.S. Appl. No. 12/577,091.

Office Action dated Oct. 28, 2010 for U.S. Appl. No. 12/577,092.

Office Action dated Oct. 29, 2010 for U.S. Appl. No. 12/577,090.

Office Action dated Nov. 1, 2010 for U.S. Appl. No. 12/577,096.

Ojida, et al. Stereocontrolled synthesis of (1S)-1-(1H-imidazol-4-yl)-1-(6-methoxy-2-naphthyl)-2-methylpropan-1-ol as a potent C17,20-lyase inhibitor. Tetrahedron: Asymmetry. 2004; 15L1555-1559.

(56) References Cited

OTHER PUBLICATIONS

Picard, et al. Synthesis and evaluation of 2'-substituted 4-(4'-carboxy- or 4'carboxymethylbenzylidene)-N-acylpiperidines: highly potent and in vivo active steroid 5alpha-reductase type 2 inhibitors. J Med Chem. Aug. 1, 2002;45(16):3406-17.
Potter, et al. A convenient, large-scale synthesis of abiraterone acetate [3B-acetoxy-17-(3-pryidyl)androsta-5,16-diene], a potential new drug for the treatment of prostate cancer. Organic Preparations and Procedures Int. 1997; 29(1):123-134.
Potter, et al. Novel steroidal inhibitors of human cytochrome P45017 alpha (17 alpha-hydroxylase-C17,20-lyase): potential agents for the treatment of prostatic cancer. J Med Chem. Jun. 23, 1995;38(13):2463-71.
Randimbivololona, et al. tabolism and excretion in bile of SC4453, a new semi-synthetic derivative of digoxin following an i.v. bolus injection in the guinea-pig. J Pharmacol. Jan.-Mar. 1984;15(1):53-64.
Recanatini, et al. A new class of nonsteroidal aromatase inhibitors: design and synthesis of chromone and xanthone derivatives and inhibition of the P450 enzymes aromatase and 17 alpha-hydroxylase/C17,20-lyase. Med Chem. Mar. 1, 2001;44(5):672-80.
Ru, et al. Synthesis and Pharmacological Activity of some 17-[2'substituted)-4'-pyrimidyl] androstene derivativies as inhibitors of human 17alpha-hydroxylase/C17,20-lyse., J. Chin. Pharm. Sci., Jun. 2001, vol. 10, No. 1, pp. 3-8.
Schayowitz, et al. Synergistic effect of a novel antiandrogen, VN/124-1, and signal transduction inhibitors in prostate cancer progression to hormone independence in vitro. Mol Cancer Ther. Jan. 2008;7(1):121-32.
Small, et al. Ketoconazole retains activity in advanced prostate cancer patients with progression despite flutamide withdrawal. J Urol. Apr. 1997;157(4):1204-7.
Souillac, et al. Characterization of Delivery Systems, Differential Scanning Calorimetry in Encyclopedia of Controlled Drug Delivery, 1999, John Wiley & Sons, pp. 212-227.
Supplementary European Search Report dated Jul. 29, 2009 for European Application No. EP 06736460.
Thompson, et al. Androgen antagonist activity by the antioxidant moiety of vitamin E, 2,2,5,7,8-pentamethyl-6-chromanol in human prostate carcinoma cells. Mol Cancer Ther. Aug. 2003;2(8):797-803.
Tindall, et al. Symposium on androgen action in prostate cancer. Cancer Res. Oct. 1, 2004;64(19):7178-80.
Trachtenberg, et al. Ketoconazole: a novel and rapid treatment for advanced prostatic cancer. J Urol. Jul. 1983;130(1):152-3.
Vasaitis, et al. Androgen Receptor Inactivation Contributes to Antitumor Efficacy of CYP17 Inhibitor VN/124-1 in Prostate Cancer. Mol. Cancer Therapeutics. 2008; 7(8):2348-2357.
Vasaitis, et al. The Effects of Novel Anti-Androgens on Androgen Receptor Action and Expression. Proceedings of the American Association for Cancer Research. 2006; 47:Abstract 5340. http://aacrmeetingabstracts.org/cgi/content/abstract/2006/1/252-d.
Vippagunta, et al. Crystalline solids. Adv Drug Deliv Rev. May 16, 2001;48(1):3-26.
Zhang, et al. A small composite probasin promoter confers high levels of prostate-specific gene expression through regulation by androgens and glucocorticoids in vitro and in vivo. Endocrinology. Dec. 2000;141(12):4698-710.
Abstract of NIH Grant Project Reference No. 5RO1 CA27440-24, approximate date Feb. 20, 2003; approximate award date Jun. 3, 2003.
Abstract of NIH Grant Project Reference No. 2R01 CA27440-25A1, approximate submission date Feb. 18, 2004; approximate award date Sep. 23, 2004.
Abstract of NIH Grant Project Reference No. 3RO1 CA27440-22S1, approximate date Jun. 21, 2001; approximate award date Aug. 17, 2001.
Abstract of NIH Grant Project Reference No. 3RO1 CA27440-23S1, approximate date May 3, 2002; approximate award date Jun. 21, 2002.
Abstract of NIH Grant Project Reference No. 5RO1 CA27440-23, approximate date Jan. 21, 2002; approximate award date Apr. 29, 2002.
Abstract of NIH Grant Project Reference No. 5RO1 CA27440-24S1, approximate date Apr. 1, 2003; approximate award date Jun. 3, 2003.
Abstract of NIH Grant Project Reference No. 5RO1 CA27440-26, approximate submission date Jul. 1, 2005; approximate award date Aug. 2, 2005.
Abstract of NIH Grant Project Reference No. 5RO1CA27440-27, approximate submission date Apr. 26, 2006.
Denmeade, et al. The SERCA pump as a therapeutic target: making a "smart bomb" for prostate cancer. Cancer Biol Ther. Jan. 2005;4(1):14-22. Epub Jan. 23, 2005.
Hartley, et al. Endoplasmic reticulum stress response in an INS-1 pancreatic beta-cell line with inducible expression of a folding-deficient proinsulin. BMC Cell Biol. Jul. 26, 2010;11:59. doi: 10.1186/1471-2121-11-59.
Lai, et al. Endoplasmic reticulum stress: signaling the unfolded protein response. Physiology (Bethesda). Jun. 2007;22:193-201.
Nawrocki, et al. Bortezomib sensitizes pancreatic cancer cells to endoplasmic reticulum stress-mediated apoptosis. Cancer Res. Dec. 15, 2005;65(24):11658-66.
NIH Grant Project Reference No. 2RO1 CA27440-24A1, 2R01 CA27440-25A1 Revised Grant Renewal Application, approximate submission date Feb. 18, 2004; approximate award date Sep. 23, 2004.
NIH Grant Project Reference No. 3RO1 CA27440-22S1 Grant Application for Supplemental Funding, approximate date Jun. 21, 2001; approximate award date Aug. 17, 2001.
NIH Grant Project Reference No. 3RO1 CA27440-23S1 Grant Continuation Application and Progress Report, approximate date May 3, 2002; approximate award date Jun. 21, 2002.
NIH Grant Project Reference No. 5RO1 CA27440-23 Grant Continuation Application and Progress Report, approximate date Jan. 21, 2002; approximate award date Apr. 29, 2002.
NIH Grant Project Reference No. 5RO1 CA27440-24 Grant Continuation Application and Progress Report, approximate date Feb. 20, 2003; approximate award date Jun. 3, 2003.
NIH Grant Project Reference No. 5RO1 CA27440-24S1 Grant Continuation Application and Progress Report, approximate date Apr. 1, 2003; approximate award date Jun. 3, 2003.
NIH Grant Project Reference No. 5RO1 CA27440-25 Grant Renewal Application, approximate submission date Jun. 26, 2003.
NIH Grant Project Reference No. 5RO1 CA27440-26 Grant Continuation Application and Progress Report, approximate submission date Jul. 1, 2005; approximate award date Aug. 2, 2005.
NIH Grant Project Reference No. 5RO1 CA27440-27 Grant Continuation Application and Progress Report, approximate submission date Apr. 26, 2006.
NIH Grant Project Reference No. 5RO1CA27440-27 ESNAP Report, approximate submission date May 8, 2006.
Office Action dated Oct. 5, 2011 for U.S. Appl. No. 12/577,094.
Rahmani, et al. The kinase inhibitor sorafenib induces cell death through a process involving induction of endoplasmic reticulum stress. Mol Cell Biol. Aug. 2007;27(15):5499-513. Epub Jun. 4, 2007.
Ron, et al. Signal integration in the endoplasmic reticulum unfolded protein response. Nat Rev Mol Cell Biol. Jul. 2007;8(7):519-29.
Wu, From acute ER stress to physiological roles of the Unfolded Protein Response. Cell Death Differ. Mar. 2006;13(3):374-84.
Skryma, et al. Store depletion and store-operated Ca2+ current in human prostate cancer LNCaP cells: involvement in apoptosis. J Physiol. Aug. 15, 2000;527 Pt 1:71-83.

\* cited by examiner

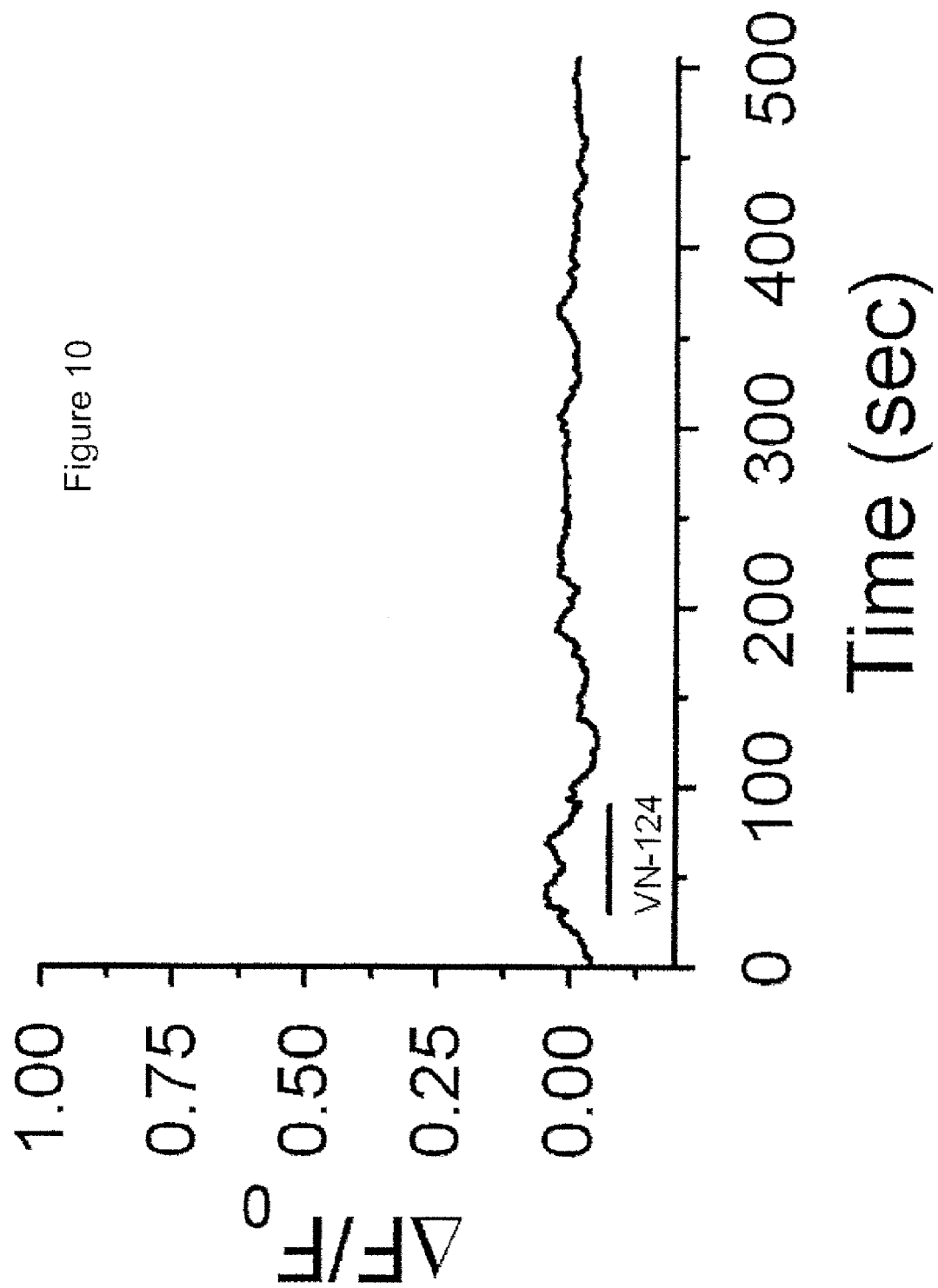

COMPOSITIONS AND METHODS OF INDUCING ENDOPLASMIC RETICULUM STRESS RESPONSE FOR THE TREATMENT OF CELL PROLIFERATIVE DISEASES

CROSS-REFERENCE TO RELATED APPLICATIONS

The present application is a U.S. National Phase Application of International Application No. PCT/US2009/040448 (filed 14 Apr. 2009) which claims priority to U.S. Provisional Application No. 61/044,621, filed 14 Apr. 2008, all of which are hereby incorporated by reference in their entirety.

STATEMENT REGARDING FEDERALLY SPONSORED RESEARCH OR DEVELOPMENT

Part of the work performed during development of this invention utilized U.S. Government funds under National Institutes of Health Grant Numbers CA117991, CA027440 and ES007263. The U.S. Government has certain rights in this invention.

BACKGROUND OF THE INVENTION

1. Field of the Invention

The present invention provides methods of inducing cell cycle arrest and/or cell growth inhibition, with the methods comprising administering to the cells an effective dose of a compound of the present invention.

2. Background of the Invention

Prostate cancer is the most common malignancy, and second leading cause of cancer related deaths in men in the western world. Despite advances in screening and treatment of localized disease, advanced prostate cancer, to date, remains incurable.

It is well-established that androgens play a vital role in the development, growth, and progression of prostate cancer. Therefore, androgen deprivation therapy (ADT) remains the standard treatment for advanced prostate cancer. Current ADT includes treatment with luteinizing hormone releasing hormone (LHRH) agonists and/or androgen receptor (AR) antagonists. Unfortunately, agonists fail to inhibit release of adrenal androgens and AR antagonists have been shown to act as partial agonists in prostate cancer cells expressing mutated and/or over-expressed AR. See Chen C. D., ez al., *Nat. Med.*, 10(1):33-9 (2004) and Fuse H, et al., *Prostate*, 67(6):630-7 (2007), which are incorporated by reference.

An alternative strategy for ADT is the global inhibition of androgen synthesis. This can be accomplished through the inhibition of the enzyme 17α-hydroxlase-$C_{17,20}$-lyase (CYP17) which catalyzes the last two reactions in the production of androgens. The imidazole anti-fungal agent, ketoconazole, which is a non-specific cytochrome P450 inhibitor, has been used for prostate cancer treatment and has shown modest efficacy in patients no longer responding to anti-androgen treatment. See Small E. J., et al., *J. Urol.*, 157(4): 1204-7 (1997) and Trachtenberg J., et al., *J. Urol.*, 130(1): 152-3 (1983), which are incorporated by reference.

Ketoconazole treatment is, unfortunately, limited by its toxicity due to the lack of specificity for CYP17. Specific CYP17 inhibitors, however, are emerging as a promising new class of anti-prostate cancer agents. One such CYP17 inhibitor, abiraterone (17-(3-pyridyl)androsta-5,16-dien-3β-ol), has entered Phase II clinical trials where it has demonstrated efficacy in castration refractory prostate cancer patients. The inventors have discovered that VN/124-1, and structurally related CYP17 inhibitors, including abiraterone, are capable of inhibiting the growth of androgen independent cell lines, such as PC-3 and DU-145. The inventors also report the discovery that, unexpectedly, these CYP17 inhibitors induce the endoplasmic reticulum stress response (ERSR) as their mechanism of action with respect to growth inhibition. Importantly, these effects were seen at concentrations previously shown to be achievable in both plasma and within tumors in mouse prostate cancer xenograft models.

The endoplasmic reticulum (ER), which is a center of protein-folding within a cell, is extremely sensitive to disruptions in homeostasis, including disruptions in calcium concentrations. Such disruptions can induce the which also referred to as the unfolded protein response. The ERSR is an evolutionarily conserved pathway that seeks to relieve the build-up of unfolded proteins in the ER. To reduce levels of unfolded proteins in the cell, the cell first up-regulates ER-resident molecular chaperones such as glucose-regulated protein 78 (gp78/BiP), and reduces ER load through phosphorylation of the α subunit of the eukaryotic translation initiation factor 2 (eIF2α). Phosphorylation of eIF2α results in attenuation of translation of non-essential proteins, including growth related proteins such as cyclin D1 Though the ERSR is a survival pathway, prolonged stimulation of the ERSR results in growth arrest and apoptosis via the up-regulation of apoptotic-related proteins including the CCAAT/enhancer-binding protein homologous transcription factor (CHOP). As a result, the ERSR has been implicated in the anti-cancer activities of many synthetic and natural cancer therapeutics including clotrimazole, fatty acid synthase inhibitors, cox-2 inhibitors, 3131-diindolylmethane, and eicosapentaenoic acid.

We demonstrate that VN/124-1 induces the ERSR in cells resulting in the up-regulation of ERSR associated genes and the phosphorylation of eIF2α. This up-regulation of ERSR associated genes and phosphorylation of eIF2α leads to the inhibition of Cyclin D1 translation, which, in turn, results in G1 arrest of the cells. Analysis of intracellular calcium signaling reveals that VN/124-1 causes the release of $Ca^{2+}$ from the ER resulting in the depletion of ER calcium stores, and a sustained rise in intracellular $Ca^{2+}$ concentrations ($[Ca^{2+}]_i$).

Accordingly, VN/124-1 and related compounds hold promise for use in methods for arresting cells during cell cycle and inhibiting cell proliferation. Such methods may be employed in treating patients that have conditions associated with abnormal cell proliferation, such as cancer.

SUMMARY OF THE INVENTION

The present invention provides methods of inducing cell cycle arrest and/or cell growth inhibition, with the methods comprising administering to the cells an effective dose of a compound of Formula I,

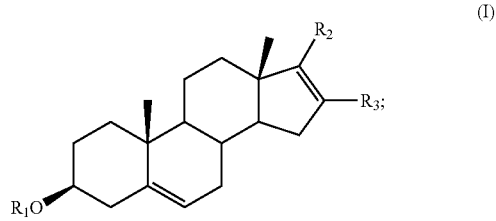

wherein $R_1$ is nothing, a hydrogen or acetyl;
$R_2$ is an azole or benzazole;
$R_3$ is a hydrogen or CHO, wherein administration of the effective dose of the compound to the cells will induce apoptosis in the cells.

In one embodiment, the methods comprise administering the compound of Formula II to the cells,

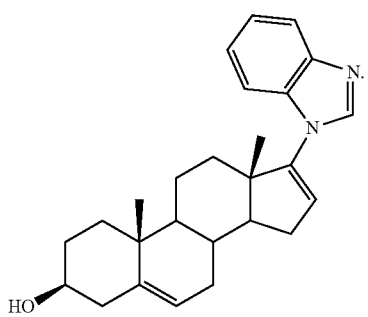

(II)

The present invention provides methods of inducing release of calcium from endoplasmic reticulum (ER) stores from cells, with the methods comprising administering to the cells an effective dose of the compound of Formula I,

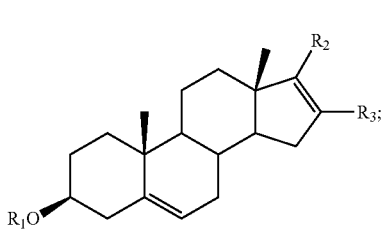

(I)

wherein $R_1$ is nothing, a hydrogen or acetyl;
$R_2$ is an azole or benzazole;
$R_3$ is a hydrogen or CHO,
wherein administration of the effective dose of the compound to the cells will induce apoptosis in the cells.

In one embodiment, the methods comprise administering the compound of Formula II to the cells,

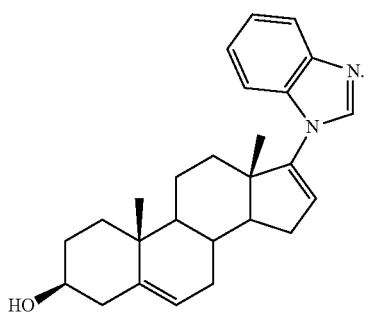

(II)

BRIEF DESCRIPTION OF THE DRAWINGS

FIG. 10 depicts PC-3 cells were pretreated for 5 minutes with cyclopiazonic acid (CPA) prior to dosing with 20 μM VN/124-1. For all treatments, $Ca^{2+}$ transients were measured in individual cells (n=9, 12, 9, respectively) as described herein.

DETAILED DESCRIPTION OF THE INVENTION

Figure 1:
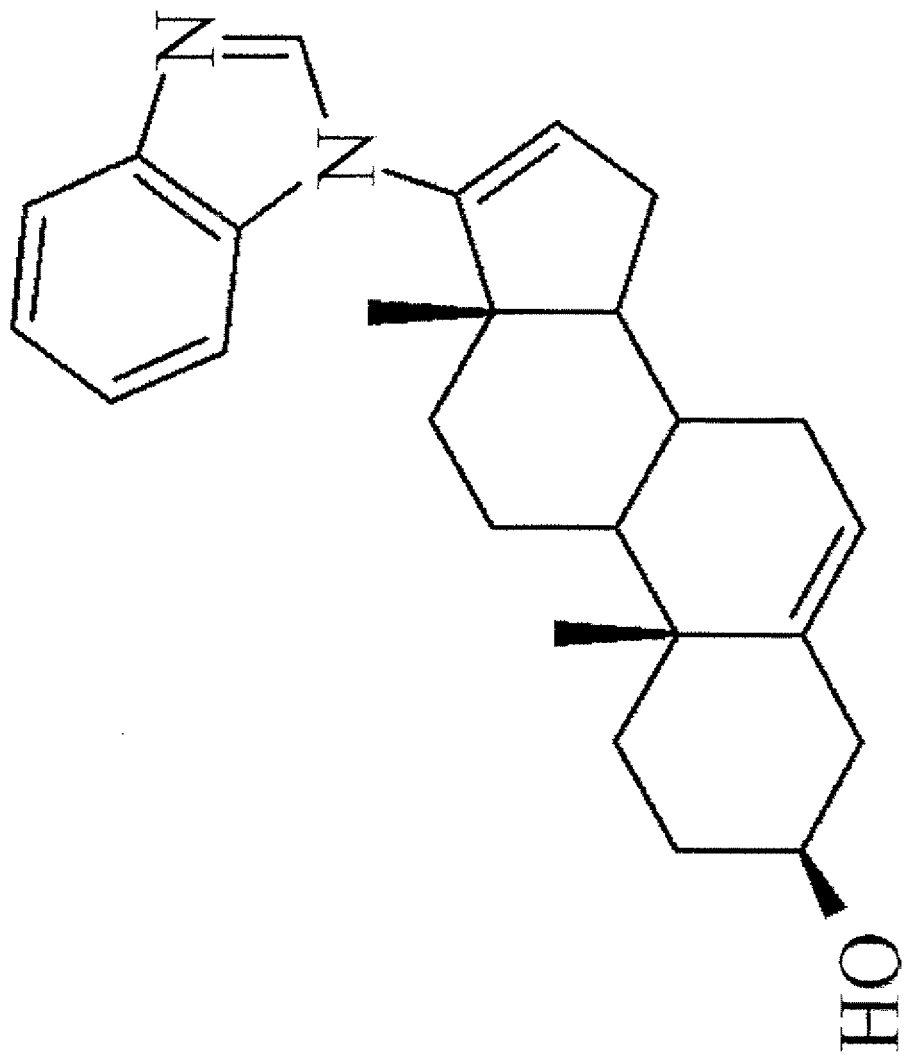
FIG. 1 depicts the structure of VN/124-1.

The present invention provides methods of inducing cell cycle arrest and/or cell growth inhibition, with the methods comprising administering to the cells an effective dose of a compound of Formula I,

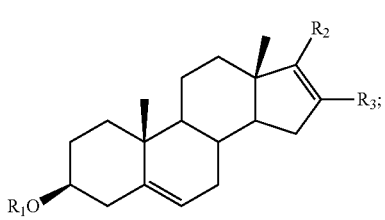

(I)

wherein $R_1$ is nothing, hydrogen or acetyl;

$R_2$ is an azole or benzazole;

$R_3$ is a hydrogen or CHO, wherein administration of the effective dose of the compound to the cells will induce apoptosis in the cells.

In one embodiment, $R_1$ is an acetyl group ($CH_3CO$). In another embodiment, $R_1$ is hydrogen. In other embodiment, R1 is nothing, such that the oxygen is double-bonded to the ring structure. Of course, as one of skill in the art would recognize, the double bond between the oxygen and the ring structure (if $R_1$ is absent) would be parallel to the rest of the ring structure.

As used herein, the term azole is used to mean a five-membered ring compound containing at least one nitrogen. Examples of azoles include, but are not limited to, pyrrole, pyrazole, imidazole, 1,2,3-triazole, 2,4-triazole tetrazole, and pentazole. Azoles also include five-membered rings with other heteroatoms, in addition to nitrogen. For example, azole, as used in the present invention, includes but is not limited to, oxazole, isoxazole, thiazole, isothiazole and the like.

In one embodiment, of the methods of the present invention. $R_2$ of the compound of Formula I is pyrrole. In another embodiment, of the methods of the present invention, $R_2$ of the compound of Formula I is pyrazole. In another embodiment, of the methods of the present invention, $R_2$ of the compound of Formula I is imidazole. In another embodiment, of the methods of the present invention, $R_2$ of the compound of Formula I is 1,2,3-triazole. In another embodiment, of the methods of the present invention, $R_2$ of the compound of Formula I is 1,2,4-triazole. In another embodiment, of the methods of the present invention, $R_2$ of the compound of Formula I is tetrazole. In another embodiment, of the methods of the present invention, $R_2$ of the compound of Formula I is pentazole.

As used herein a benzazole is a double-ringed structure comprising a benzene or substituted benzene ring fused to an azole ring. Examples of benzazoles also include, but are not limited to, benzpyrroles, benzpyrazoles, benzimidazoles, henztriazoles, benzoxazoles, benzisoxazoles, benzthiazoles and benzisothiazoles. In one embodiment, $R_2$ of Formula I is a benzpyrrole. In another embodiment, $R_2$ of Formula I is a benzpyrazole. In another embodiment, $R_2$ of Formula I is a benzimidazole. In another embodiment, $R_2$ of Formula I is a benztriazole. In another embodiment, $R_2$ of Formula I is a benzoxazole. In another embodiment, $R_2$ of Formula I is a benzisoxazole. In another embodiment, $R_2$ of Formula I is a benzthiazole. In another embodiment, $R_2$ of Formula I is a benzisothiazole.

In one embodiment, $R_3$ is a hydrogen. In another embodiment, $R_3$ is CHO.

In one specific embodiment, the methods of the invention comprise administering the compound of Formula II.

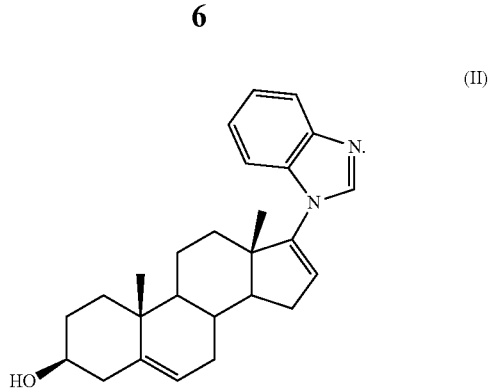

(II)

In another embodiment, the methods of the invention comprise administering at least one of the compounds of Formula III (VN/63-1), IV (VN/85-1), V (VN/125-1), which are shown below.

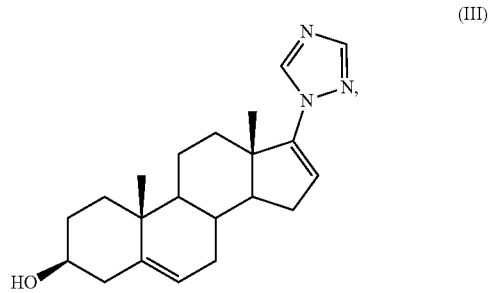

(III)

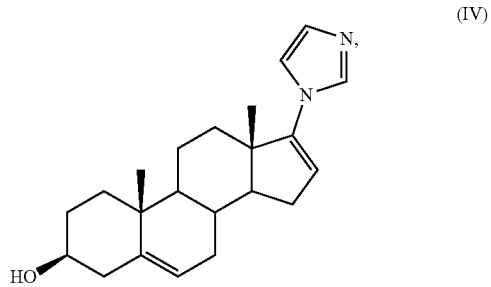

(IV)

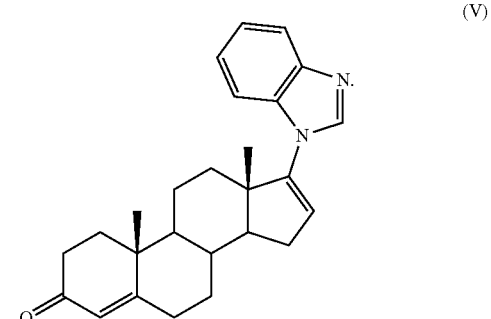

(V)

The compounds of the present invention are administered to cells in an effective amount to induce cell cycle arrest and/or cell growth inhibition in the cells to which the compounds are administered. The compounds of the present invention can also be administered to cells in an effective amount to induce apoptosis in the cells to which the compounds are administered. As used herein, the cells can be in culture or can be part of a tissue, organ or organism, such as, but not limited to a human. The cells may be normal or abnormal, such as, but not limited to, malignant or benign cancer cells. Thus, in one embodiment, the compound is administered to neoplastic cells in an organism. In a specific embodiment, at least one compound of the present invention is administered to neoplastic prostate cells. The prostate cells may or may not be responsive to androgen deprivation therapy. In another embodiment, the compounds are administered to neoplasms, such as, but not limited to, neoplasms of the blood-forming organs, the liver, pancreas, thyroid, andrenals, pituitary, ovaries, testicles, breast, central nervous system (including brain, spinal column), bone, connective tissue, lungs, the gastrointestinal system (esophagus, stomach, colon, rectum, etc.), connective tissue, uterus, mucous membranes, mouth and tongue, the lining of the peritoneum, the lymphatics and sensory organs.

As used herein, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular.

As used herein, the term "administer" or "administering" is used to mean introducing at least one compound to a cell or group of cells, such that the compound can exert a biological effect of the cell or group of cells. Thus, administration may be in the form of dosing an organism with the compound, such that the organism's circulatory system will deliver the compound to the target cell or cells. Administration may also mean that the compound is placed in direct contact with the cell or group of cells, such as topical administration of the compound, or direct injection of the compound. Administration may also mean placing the compound in cell culture medium and placing the cell or group of cells in contact with the dosed cell culture medium.

In one embodiment, "treatment" or "treating" refers to an amelioration of a disease or disorder, or at least one discernible symptom thereof, preferably associated abnormal cell proliferation, such as cancer. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g. stabilization of a physical parameter, or both. In yet another embodiment, "treatment" or "treating" refers to delaying the onset of a disease or disorder or delaying the onset of a physical parameter or symptom. In one specific embodiment, treatment refers to the application of the methods of the present invention to reduce, stall, or inhibit the growth of or proliferation of tumor cells. In another specific embodiment, treatment refers to the application of the methods of the present invention to induce apoptosis in tumor cells. The tumor cells may or may not respond to androgen deprivation therapy. In another specific embodiment, the tumor cells are androgen independent cells. In a further embodiment, the androgen independent tumor cells are prostate cancer cells.

When administration is for the purposes of "preventing" abnormal cell proliferation, ("prophylactic administration"), the substance is provided in advance of any visible or detectable symptom. The prophylactic administration of the substance serves to attenuate subsequently arising symptoms or physical parameters or reduce the possibility of symptoms from arising altogether. Thus, as used herein, the term "prevent" as used in connection with administering the compounds of the present invention, is used to indicate the timing of the administration, i.e., before a detectable symptom arises, rather than indicate a complete removal of the possibility of developing a condition associated with abnormal cell proliferation.

The invention encompasses compounds that are effective in inducing ERSR both in vivo and in vivo. The inventors have surprisingly found that the compounds of the invention are effective in inducing ERSR, via calcium release from the ER stores, among other mechanisms. Without being limited by theory, it is believed that modulation of ERSR may be useful in treating conditions where cells are already under a low level ER stress, such as tumor cells. The invention further encompasses compositions and formulations comprising one or more compounds that are useful in modulating ERSR. The invention also encompasses methods of modulating ERSR in cells comprising administering to the cells, for example mammalian cells an effective amount of an agent to induce ERSR. In an illustrative embodiment, the agent for inducing ERSR is a compound of the invention.

In one embodiment, a composition of the invention comprising a compound of the invention and a pharmaceutically acceptable vehicle, is administered to a mammal, preferably a human, in need of treatment, wherein the treatment comprises inducing ERSR in select cells in the subject. In one specific embodiment, the select cells that undergo ERSR are under a low level ER stress prior to administration of the compounds or compositions of the present invention.

In another illustrative mode of the embodiment, the compositions of the invention are administered as a preventative measure to a patient having a non-genetic predisposition to abnormal cell proliferation. Accordingly, the compositions of the invention may be used for the prevention of one disease or disorder and concurrently treating another disorder.

In another embodiment, at least one compound of the present invention is coadministered with at least one additional agent that induces at least a low-level ER stress on the cells. Examples of compounds that induce ER stress in cells include, but are not limited to, cisplatin, gentamicin, bortezomib, eeyarestatin I (EerI), sorafenib, N-3 PUFAs, such as, but not limited to, docosahexaenoic acid (DHA), imatinib, disulliram and derivatives thereof as disclosed in U.S. Pat. No. 6,288,110, which is incorporated by reference, epigallocatechin gallate (EGCG), anti-GRP78 antibody and nelfinavir, to name a few. Of course, the compounds of Formulas I-V as disclosed herein may be coadministered with one another in lieu of or in addition to other compounds listed herein that induce ER stress.

The term "coadminister" indicates that each of at least two compounds is administered during a time frame wherein the respective periods of biological activity or effects overlap. Thus the term includes sequential as well as coextensive of the compounds of the present invention. And similar to administering compounds, coadministration of more than one substance can be for therapeutic and/or prophylactic purposes. If more than one substance is coadministered, the routes of administration of the two or more substances need not be the same. The scope of the invention is not necessarily limited by the identity of the substance which may be coadministered.

Any of the compounds disclosed in the present invention may be conjugated to an antibody that is targeted for a specific antigen on a cell. The use of antibody-drug conjugates (ADC), "immunoconjugates," for the local delivery of cytotoxic or cytostatic agents, i.e. drugs to kill or inhibit tumor cells in the treatment of cancer or abnormal cell growths will allow targeted delivery of the drug moiety to tumors or abnormal growths. Such methods on conjugating an antibody to an active compound are disclosed in Lambert, J., *Curr. Opinion* in *Pharmacology* 5:543-549, (2005), Wu et al., *Nature Biotechnology* 23(9):1137-1146, (2005), Payne, G., *Cancer Cell* 3:207-212, (2003), Syrigos and Epenetos, *Anticancer Research* 19:605-614 (1999), Niculescu-Duvaz and Springer, *Adv. Drug Del. Rev.* 26:151-172, (1997), Baldwin et al., *Lancet*: March 15; 1(8481):603-05 (1986), Thorpe, "Antibody Carriers Of Cytotoxic Agents In Cancer Therapy: A Review," in Monoclonal Antibodies '84: Biological And Clinical Applications, A. Pinchera et al (ed.s), pp. 475-506 (1985), and U.S. Pat. No. 4,975,278, all of which are incorporated by reference. ADCs also allow intracellular accumulation in cells of interest, e.g., tumor cells, and may also allow administration of the active compounds, where systemic administration of these unconjugated drug agents may result in unacceptable levels of toxicity to normal cells. Efforts to improve the therapeutic index, i.e., maximal efficacy and minimal toxicity, of ADC have focused on the selectivity of polyclonal (Rowland et al., *Cancer Immunol. Immunother.*, 21:183-87 (1986)) and monoclonal antibodies (mAbs) as well as drug-linking and drug-releasing properties (Lambert, J., *Curr. Opinion in Pharmacology* 5:543-549 (2005)).

For example, the compounds of the present invention may be conjugated to an anti-PSMA antibody (prostate specific membrane antigen) through, thr example, the —$OR_1$— at the 3 position of the compounds of Formula I. Other antibodies are well-known in the art and could be employed in the methods of the present invention.

Due to the activity of the compounds of the invention, the compounds are advantageously useful in veterinary and human medicine. As described above, the compounds of the invention are useful for the treatment or prevention of diseases and disorders associated with abnormal cell proli aeration.

The invention provides methods of treatment and prophylaxis by administration to a patient of a therapeutically effective amount of a composition comprising a compound of the invention. The patient can be a mammal, including, but not limited, to an animal such a cow, horse, sheep, pig, cat, dog, mouse, rat, rabbit, guinea pig, etc., and a human or non-human primate.

The present compositions, which comprise one or more compounds of the invention, can be administered orally. The compounds of the invention may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend, in part, upon the site of the medical condition. In most instances, administration will result in the release of the compounds of the invention into the bloodstream.

In specific embodiments, it may be desirable to administer one or more compounds of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of an atherosclerotic plaque tissue. In another embodiment, the compounds may be conjugated to an antibody that is specific towards an antigen on the abnormally proliferating cells.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

In another embodiment, the compounds of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compounds of the invention can be delivered in a controlled release system. In one embodiment, a pump may be used (see Langer, supra; Sefton, 1987, CRC Crit. Ref. Biomed. Eng. 14:201; Buchwald et al., 1980, Surgery 88:507 Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neural. 25:351; Howard et al., 1989, J. Neurosurg. 71:105). In yet another embodiment, a controlled-release system can be placed in proximity of the target of the compounds of the invention, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, Science 249:1527-1533) may be used.

The present compositions will contain a therapeutically effective amount of a compound of the invention, optionally more than one compound of the invention, in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Science and Practice of Pharmacy (21st ed., Hendrickson. R., et al., Eds., Lippincott Williams & Wilkins, Baltimore, Md. (2006)), which is incorporated by reference.

In a preferred embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. Where necessary, the compositions may also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating: the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

It is preferred that the compositions of the invention be administered orally. Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening, agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound of the invention per kilogram body weight. In specific embodiments of the invention, the oral dose is 0.01 milligram to 70 milligrams per kilogram body weight, more specifically 0.1 milligram to 50 milligrams per kilogram body weight, more specifically 0.5 milligram to 20 milligrams per kilogram body weight, and yet even more specifically 1 milligram to 10 milligrams per kilogram body weight. The dosage amounts described herein refer to individual amounts administered; that is, if more than one compound of the invention is administered, the preferred dosages correspond to the individual amount of the compounds of the invention administered.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention. In another embodiment, the kit comprises a compound of the invention and another ER stress-inducing compound, including but not limited to those disclosed herein.

The examples herein are for illustrative purposes only and they are not intended to limit the scope of the invention in any way.

EXAMPLES

Materials and Methods

Cell Culture and Viability Assays

All cell lines were obtained from American. Type Culture Collection (Rockville, Md.) and maintained in RPM 1640 media supplemented with 10% fetal bovine serum and 5% penicillin streptomycin solution. Cells were grown as a monolayer in a humidified incubator (5% $CO_2$) at 37° C. To determine the effect of the various compounds on cell proliferation, cells were plated (2500 cells/well) in 96-well cell culture dishes (Corning, Inc. Corning, N.Y.). After a 24 hr attachment period, media was replaced with fresh media containing compounds (0.01 μM-100 μM) or vehicle (95% ethanol). The cells were then allowed to grow in the presence of the drugs for 96 hrs. After 96 hrs, relative cell viability was assessed using the MIT reagent (3-(4,5-dimethylthiazol-2-yl)-2,5-diphenyltetrazolium bromide) as is well-known in the art. Experiments were carried out 3 times with 6 replicates per dose per experiment (n=18). Results were plotted using the average of each dose over all three experiments and fitted with a best-fit sigmoidal dose response variable slope curve using GraphPad Prism 4.01 (GraphPad Software, Inc.). For combination of VN/124-1 and Thapsigargin, cells were treated for 72 hrs and viability was assessed as described for single agents. Combination index (CI) was calculated as is well known in the art, and CI values less than 1 are considered synergistic.

To perform the microarray experiments, PC-3 cells were treated with (95% ethanol) or 20 μM of VN/124-1. After 24 hr exposure to the agent, cells were pelleted and lysed using Qiagen RLT (Qiagen Inc.; Valencia, Calif.) buffer containing 1% β-mercaptoethanol. Total RNA was isolated using the Qiagen RNeasy-Mini Kit following manufacturer's protocol. Quantity and purity were assessed by absorption at 260 nm and 280 nm. RNA integrity was assessed using an Agilent Bioanalyzer (Agilent Technologies; Santa Clara, Calif.). Experiments were carried out in duplicate, with triplicate samples (dosed independently on 3 different days) from each experiment pooled for analysis on a single chip.

Samples were hybridized to a GeneChip® Human Genome Focus Array (Affymetrix Inc., U.S.A.) and analyzed using an Affymetrix Genechip Scanner 3000 according to manufacturer's protocol. Gene ontologies were identified using the online Database for Annotation, Visualization, and integrated Discovery (DAVID) provided by the National Institute of Allergy and Infectious Diseases and the National Institute of Health. Only genes that were up or down-regulated by an average of about 2-fold and had a minimum 1.5-fold change (up or down) per array were used for this analysis. Genes that showed less than 1.5-fold change (up or down) in control samples on one or both chips were excluded. Stringent criteria of a minimum EASE/P-Value threshold of 0.001 and a gene count threshold of 5 were used to identify altered gene ontologies.

Real-Time PCR

Cells were treated, lysed and RNA collected and quantified using the same method outlined above. Cells were dosed independently on 3 separate days (n=3). 1 μg of total RNA was converted to cDNA using ReactionReady™ First Strand cDNA Synthesis kit (SuperArray Bioscience Corp.; Frederick, Md.) following manufacturer's protocol. 50 ng of template cDNA was then used in subsequent real-time PCR (qRT-PCR) reactions. Template was combined with target gene specific or β-actin control $RT^2$ PCR Primer Sets, $RT^2$ Real-Time™ SYBR Green/Rox Master Mix (SuperArray Bioscience Corp.), and $ddH_2O$ for a final reaction volume of 25 μL and run on a 7900HT Fast Real-Time PCR system (Applied Biosystems; Foster City, Calif.) following manufacturer's protocol. Fold changes were calculated using the $\Delta\Delta C_t$ method as recommended by the manufacture's protocol.

Cell Cycle Analysis

Cells were synchronized in the G1/G0 phase by maintaining them in 0.2% FBS-containing media for 96 hrs. After starvation, media was replaced with normal growth media (10% FBS) containing vehicle (95% ethanol) or 20 μM VN/124-1 for 12, 18, and 24 hrs. At each timepoint, cells were pelleted and fixed in 70% ethanol at −20° C. for at least 24 hrs. Fixed cells were then incubated with 1 mL propidium iodide (PI) staining buffer (1 mg/ml PI, 0.1% Triton-X, and 10 μg/ml RNase A dissolved in PBS) for 1 hr at room temperature and DNA content was measured by flow cytometry analysis using a FACSort flow cytometer (Becton Dickinson, San Jose, Calif.). 15,000 events were analyzed for each sample and ModFit LT version 3.1 (Verity Software House Ind., ME) was used to analyze cell cycle distribution.

Western Blot

Cells were treated with VN/124-1, thapsigargin or vehicle for 6 and 24 hrs. Protein was isolated, subjected to SDS-PAGE, transferred and imaged as is known in the art. Primary antibodies against eIF2α, p-eIF2α, cyclin D1, gp78/BiP, and β-actin were purchased from Cell Signaling (Danvers, Mass.), Anti-CHOP antibody was purchased from Sigma Aldrich (St Louis, Mo.). Quantitation of relative protein expression was determined via densitometry using the software ImageQuant 5.0 (Molecular Dynamics) with each protein normalized to its respective loading control. Results represent the average of at least 3 independent experiments, with representative blots shown.

$Ca^{3+}$ Measurements

PC-3 Cells were loaded with either fura-2 or fluo-3 indicator by incubation with 2 μM fura-2/AM or 2 μM fluo-3/AM in RPMI 1640 medium containing 10% fetal bovine serum for >60 min at room temperature. During experiments, the coverslips were mounted in a flow chamber and superfused with oxygenated Locke solution containing (in mM): 10 glucose, 136 NaCl, 5.6 KCl, 1.2 $NaH_2PO_4$ 14.3 $NaHCO_3$, 1.2 $MgCl_2$, and 2.2 $CaCl_2$, pH 7.4, at room temperature (22-24° C.).

For measurement of $[Ca^{2+}]_i$ in individual cells, PC-3 cells were incubated on coverslips with 20 μM VN/124-1 or vehicle for 24 hrs. Cells loaded with fura-2 were placed in a perfusion chamber mounted on an inverted microscope (TE200; Nikon, Tokyo, Japan) equipped with a UV-transmitting objective (SuperFluor, 40×, N.A. 1.4, Nikon). Pura-2 was alternately excited by 340 nm and 380 nm light from monochrometers (Deltascan Illumination System, Photonic Technology International (PTI), South Brunswick, N.J.) and fura-2 emission was passed through a 515 nm longpass tiller before detection by a cooled CCD camera (Retiga 2000R, Q-Imaging, Burnaby, Canada). For measurement of $Cat^{2+}$ transients in individual cells, coverslips with fluo-3 loaded cells were excited by the output of a 100 W mercury arc lamp that passed through a 480 nm bandpass filter (30 nm bandwidth). Fluorescence emission was passed through a 515 nm longpass filter before capture by a cooled CCD camera (Retiga 2000R, Q-Imaging). Image acquisition was performed with QCapture Pro (Q-Imaging) and analysis was performed with ImageJ (U.S. National Institutes of Health Bethesda, Md. USA).

Fluo-3 $Ca^{2+}$ indicator measurements are reported as the fractional change in fluorescence intensity relative to baseline (ΔF/F0), which was determined as follows. Within a temporal sequence of fluorescence images, a region of interest (ROI) was drawn around each cell to be analyzed. The fluorescence signal from each cell was calculated as the pixel-averaged intensity within each ROI. In these experiments, we typically observed a slight downward drift in baseline, which was principally attributable to photo-bleaching of the indicator. In such cases, the drift was always well lit by a low-amplitude single-exponential decay. The fitted baseline value (F0) at every time point was then used to calculate ΔF/F0. ΔF/F0 values are reported as mean±SE. For fura-2 measurements, $[Ca^{2+}]_i$ was derived using the ratio method that is well known in the art.

Statistical Analysis qRT-PCR results for each gene were analyzed via a student's T-test comparing ΔCt values (Ct value of test gene minus α-actin control). Western blots and combination growth studies were analyzed with a Kruskal-Wallis and Dunn's multiple comparison post-hoc. Flow cytometry and $[Ca^{2+}]_i$ data was analyzed with a student's T-test.

Results

Cell Culture Results

Figure 2:
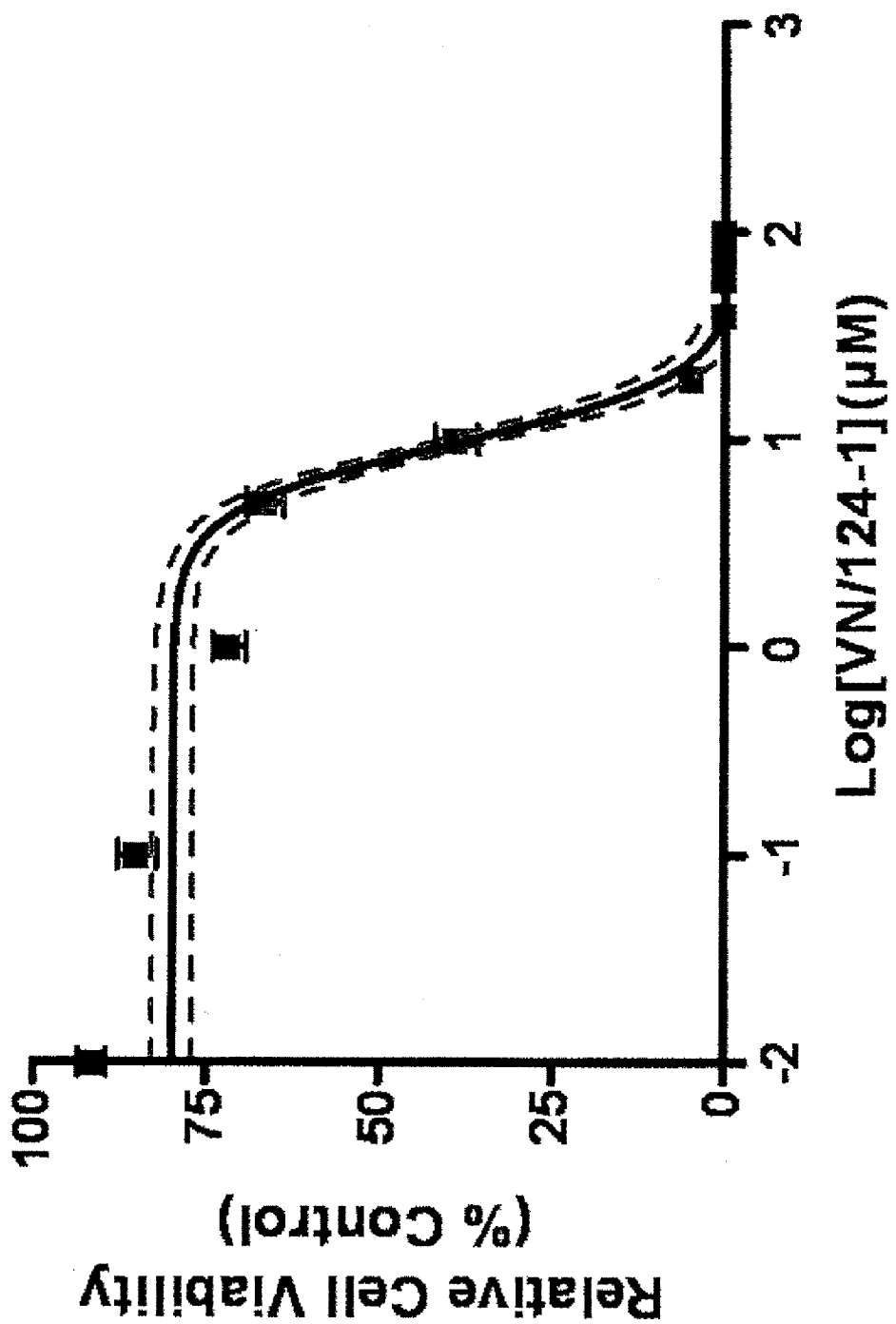
FIG. 2 depicts cell viability curves for PC-3 cells, generated from an MTT assay after 96 hour exposure to VN/124-1 as described herein. Data points represent the mean±SEM of 18 replicates from 3 independent experiments. Solid line is a best fit sigmoidal-dose response (variable slope) and dotted lines represent the 95% confidence interval.
Figure 3:
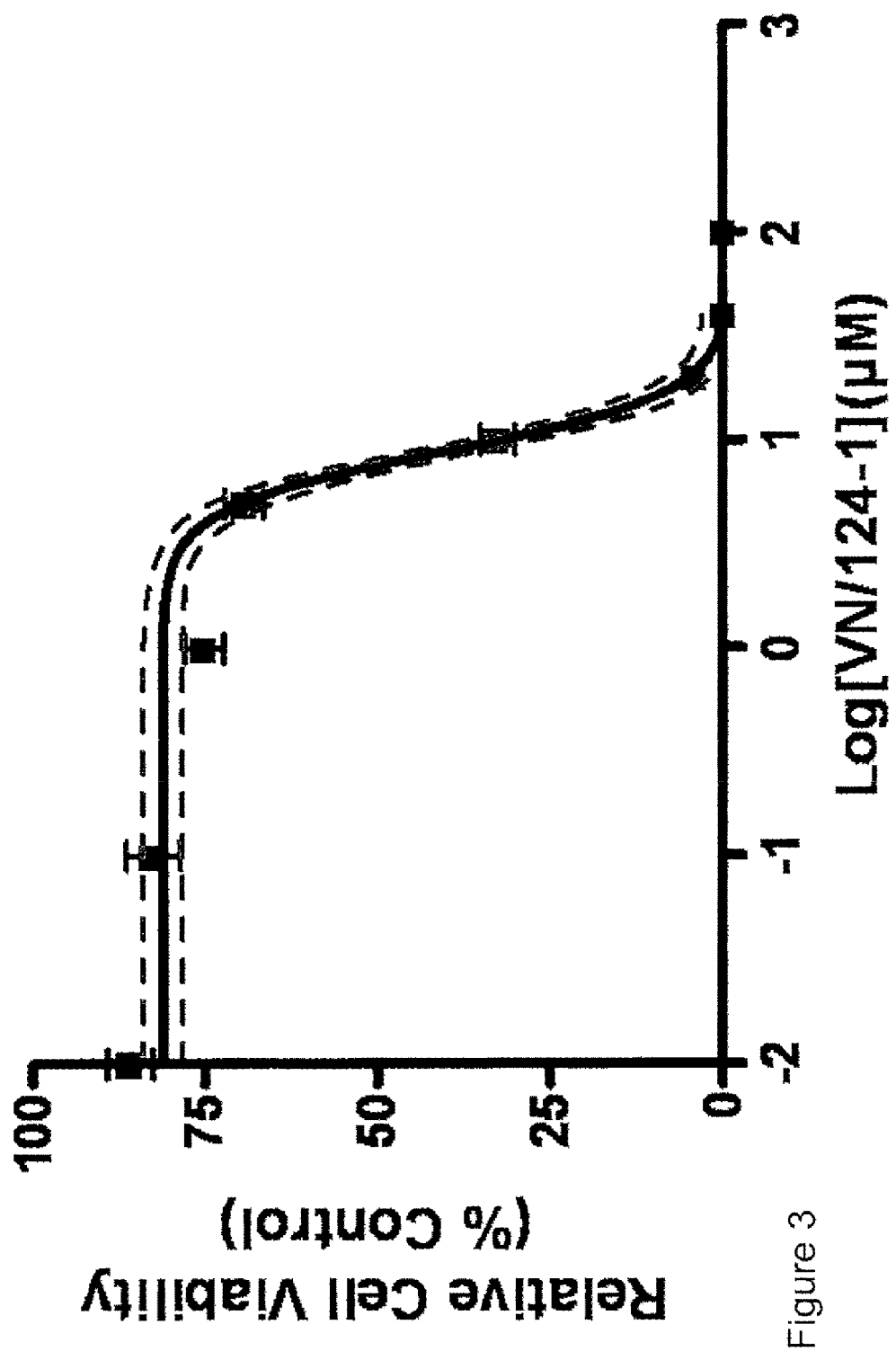
FIG. 3 depicts cell viability curves for DU-145 cells, generated from an MTT assay after 96 hour exposure to VN/124-1 as described in the materials and methods section. Data points represent the mean±SEM of 18 replicates from 3 independent experiments. Solid line is a best fit sigmoidal-dose response (variable slope) and dotted lines represent the 95% confidence interval.
Figure 4:
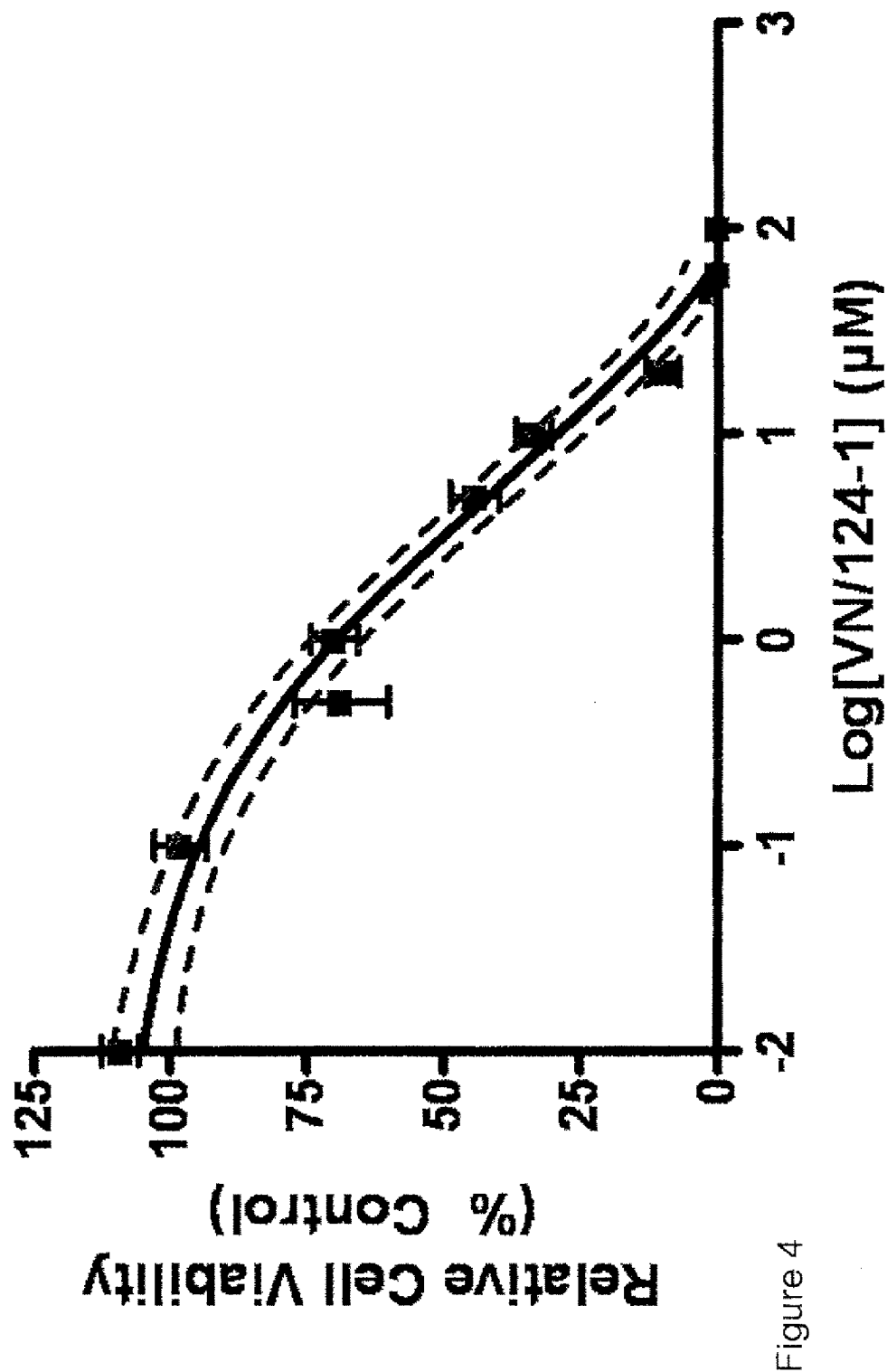
FIG. 4 depicts cell viability curves for LNCaP cells, generated from an MTT assay after 96 hour exposure to VN/124-1 as described in the materials and methods section. Data points represent the mean±SEM of 18 replicates from 3 independent experiments. Solid line is a best fit sigmoidal-dose response variable slope) and dotted lines represent the 95% confidence interval.

To determine if VN/124-1 exerted a direct cytotoxic/cytostatic effect, the androgen independent prostate cancer cell lines PC-3 and DU-145 were treated with increasing concentrations of VN/124-1, and it was found that the compound inhibited the growth of both cell lines in the low micromolar range (FIGS. 2-4 and Table 1). The potency of VN/124-1 against the growth of the PC-3 and DU-145 cell lines was comparable to that seen with androgen dependent LNCaP cells (low micromolar range). Structurally related steroidal C-17 substituted lyase inhibitors VN/63-1, VN/85-1, VN/125-1, and abiraterone, also inhibited the growth of PC-3 and DU-145 cells (Table 1). It is clear from these results that these compounds also have activity distinct from the androgen axis.

TABLE 1

Cytotoxic/Cytostatic effects of Various Compounds of the Invention

| Compound | Cell Line | $GI_{50}$ (μM) | 95% C.I. (μM) | $GI_{90}$ (μM) | 95% C.I. (μM) |
|---|---|---|---|---|---|
| VN/63-1 | PC-3 | 2.91 | 1.14-11.57 | >100 | — |
| VN/85-1 | | 1.86 | 1.31-2.86 | 30.41 | 13.18-67.61 |
| VN/124-1 | | 7.82 | 7.13-8.38 | 18.62 | 16.10-21.88 |
| VN/125-1 | | 1.41 | 1.22-1.60 | 8.07 | 6.61-9.80 |
| Abiraterone | | 9.32 | 8.69-9.94 | >100 | — |
| VN/63-1 | DU-145 | 11.04 | 4.75-22.74 | >100 | — |
| VN/85-1 | | 5.31 | 3.71-7.22 | 31.62 | 23.12-40.58 |
| VN/124-1 | | 7.55 | 6.90-8.11 | 15.95 | 13.86-18.24 |
| VN/125-1 | | 6.57 | 5.58-7.51 | 15.53 | 12.40-19.55 |
| Abiraterone | | 14.68 | 13.42-15.95 | >100 | — |
| VN/63-1 | LNCaP | 1.05 | 0.69-1.55 | >100 | — |
| VN/85-1 | | 2.47 | 1.55-3.96 | 36.49 | 23.03-58.74 |
| VN/124-1 | | 3.15 | 2.41-4.17 | 31.99 | 23.82-45.01 |
| VN/125-1 | | 1.18 | 0.95-1.48 | 13.46 | 9.80-18.01 |
| Abiraterone | | 1.41 | 0.95-1.96 | 25.12 | 14.19-100 |

$GI_{50}$ and $GI_{90}$ values were calculated from sigmoidal-dose response curves (variable slope) generated from 3 independent experiments.

Microarray Results

To shed light on the mechanism of action of VN/124-1, PC-3 cells were treated with 20 μM (~GI90) of the compound for 24 hrs and global gene expression changes were measured using a GeneChip® Human Genome Focus Array. The online database for annotation, visualization, and integrated discovery (DAVID) was used to identify clusters of related genes affected by VN/124-1. As shown in Table 2, the most enriched up-regulated ontologies were those relating to stress and metabolism, in particular amino acid metabolism. Nearly all of the down-regulated ontologies (Table 3) were associated with the cell cycle, especially S-phase (DNA replication.

TABLE 2

Genes Up-Regulated In Response to VN/124-1

| Up-regulated Ontology | Count | % | P-Value |
|---|---|---|---|
| Response to Stress | 16 | 24.24 | 1.93E−05 |
| Amino Acid Metabolism | 8 | 12.12 | 6.97E−05 |
| Amine Metabolism | 9 | 13.64 | 1.01E−04 |
| Nitrogen Compound Metabolism | 9 | 13.64 | 1.61E−04 |
| Amino Acid and Derivative Metabolism | 8 | 12.12 | 1.77E−04 |
| Negative Regulation of Biological Process | 12 | 18.18 | 1.90E−04 |
| Negative Regulation of Cellular Process | 11 | 16.67 | 4.57E−04 |
| Development | 18 | 27.27 | 6.29E−04 |
| Carboxylic Acid Metabolism | 9 | 13.64 | 7.48E−04 |
| Organic Acid Metabolism | 9 | 13.64 | 7.68E−04 |
| Response to External Stimulus | 9 | 13.64 | 9.76E−04 |

P-values were based on an enrichment (EASE) score.

TABLE 3

Genes Down-Regulated In Response to VN/124-1

| Down-Regulated Ontology | Count | % | P-Value |
|---|---|---|---|
| DNA Replication | 17 | 34.69 | 3.82E−19 |
| DNA Metabolism | 19 | 38.78 | 2.98E−13 |
| DNA-Dependent DNA Replication | 10 | 20.41 | 6.88E−12 |
| Cell Cycle | 16 | 32.65 | 1.41E−09 |
| Biopolymer Metabolism | 27 | 55.10 | 1.51E−08 |
| Regulation of Progression Through Cell Cycle | 10 | 20.41 | 9.25E−06 |
| Regulation of Cell Cycle | 10 | 20.41 | 9.41E−06 |
| Nucleobase, Nucleoside, Nucleotide and Nucleic Acid Metabolism | 24 | 48.98 | 8.12E−05 |
| Macromolecule Metabolism | 28 | 57.14 | 9.94E−05 |
| Second-Messenger-Mediated Signaling | 6 | 12.24 | 2.86E−04 |

P-values were based on an enrichment (EASE) score.

Real Time PCR Results

The most highly up-regulated gene found in the microarray was S100P calcium binding protein (S1001)). S100P is a member of the S100 family of proteins, all of which take part in $Ca^{2+}$ signaling. Surprisingly, S100P has been shown to be involved in the growth and survival of cancer cells and is known as a negative prognostic marker of disease progression. The functional significance of this remains unknown, but interestingly, S100P has been reported in the art to be up-regulated by other chemotherapeutics and natural anticancer agents including DNA cross-linking agents and all-trans retinoic acid. Other genes verified by qRT-PCR that were up-regulated in the microarray experiment include asparagines synthetase (ASKS) and activating transcription factor 4 (ATF4), both of which have been reported to be up-regulated by the CHOP was not included in the microarray, but is also marker for the ERSR and qRT-PCR revealed it to be strongly up-regulated by VN/124-1. Interestingly, cyclin D1 mRNA levels were not affected by VN/124-1 but the downstream cyclin E2 was significantly reduced. These results were identical to those seen in the microarray.

Western Blot Results

Figure 5:
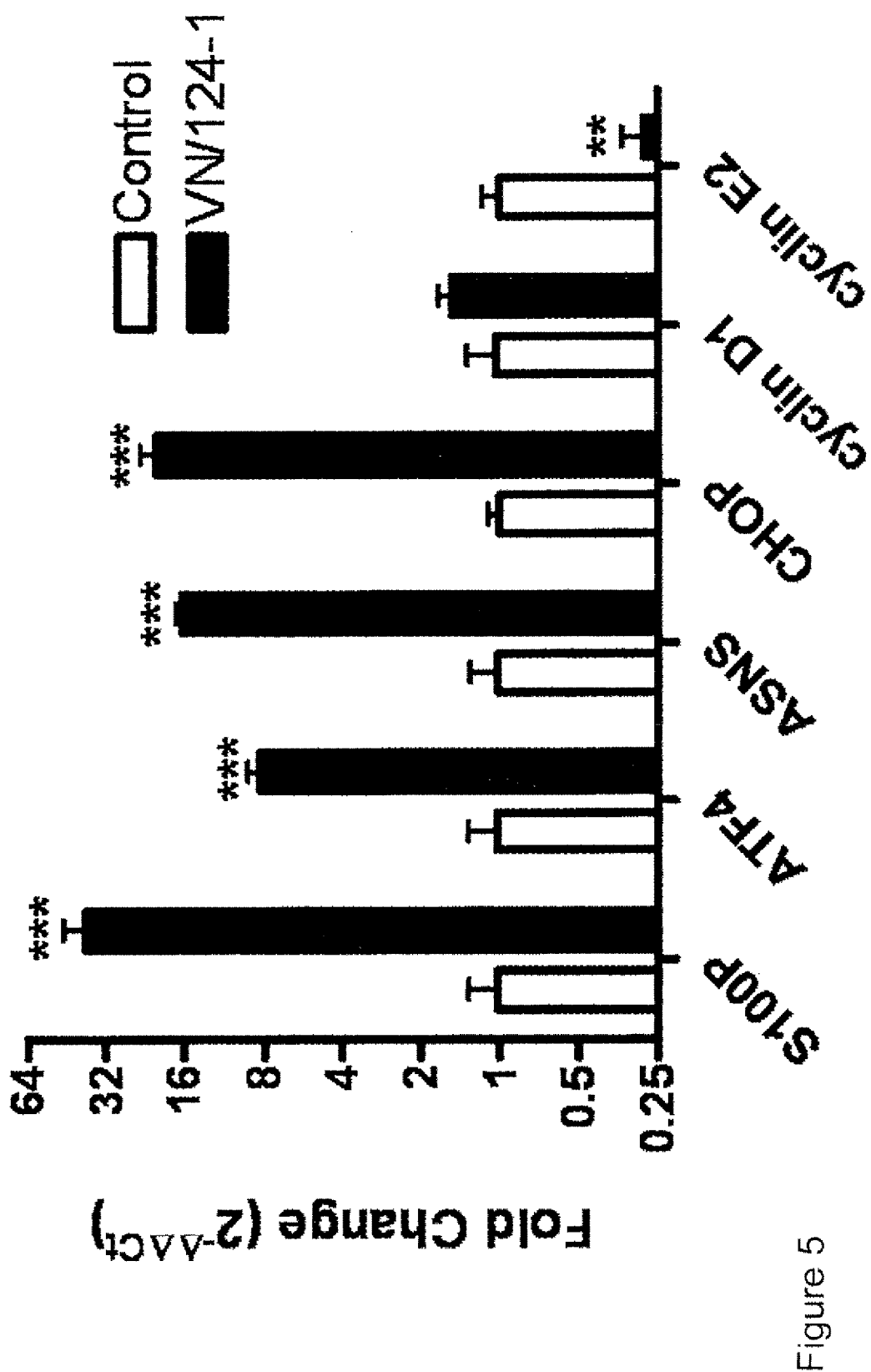
FIG. 5 depicts VN/124-1 inducing the ERSR resulting in G1G0 cell cycle arrest The figure shows qRT-PCR assessment of stress response and cell cycle related genes following 24 hr exposure to 20 μM VN/124-1. Expression is measured as fold change relative to control.
Figure 6:
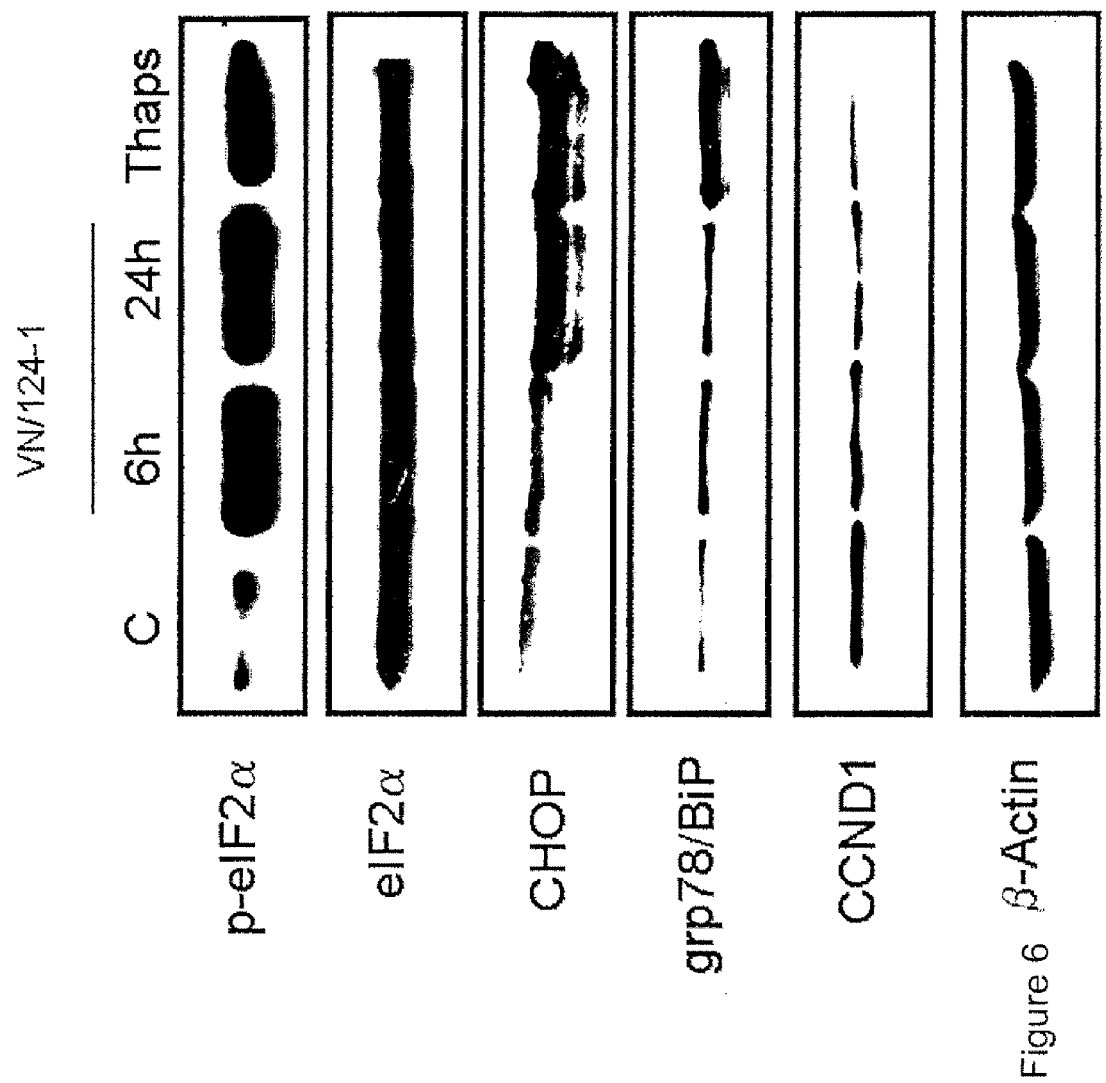
FIG. 6 depicts representative western blots following 6 and 24 hr exposure to 20 μM VN/124-1 or 6 hr exposure to 500 nM of the known ERSR-inducer thapsigargin for 6 hrs.
Figure 7:
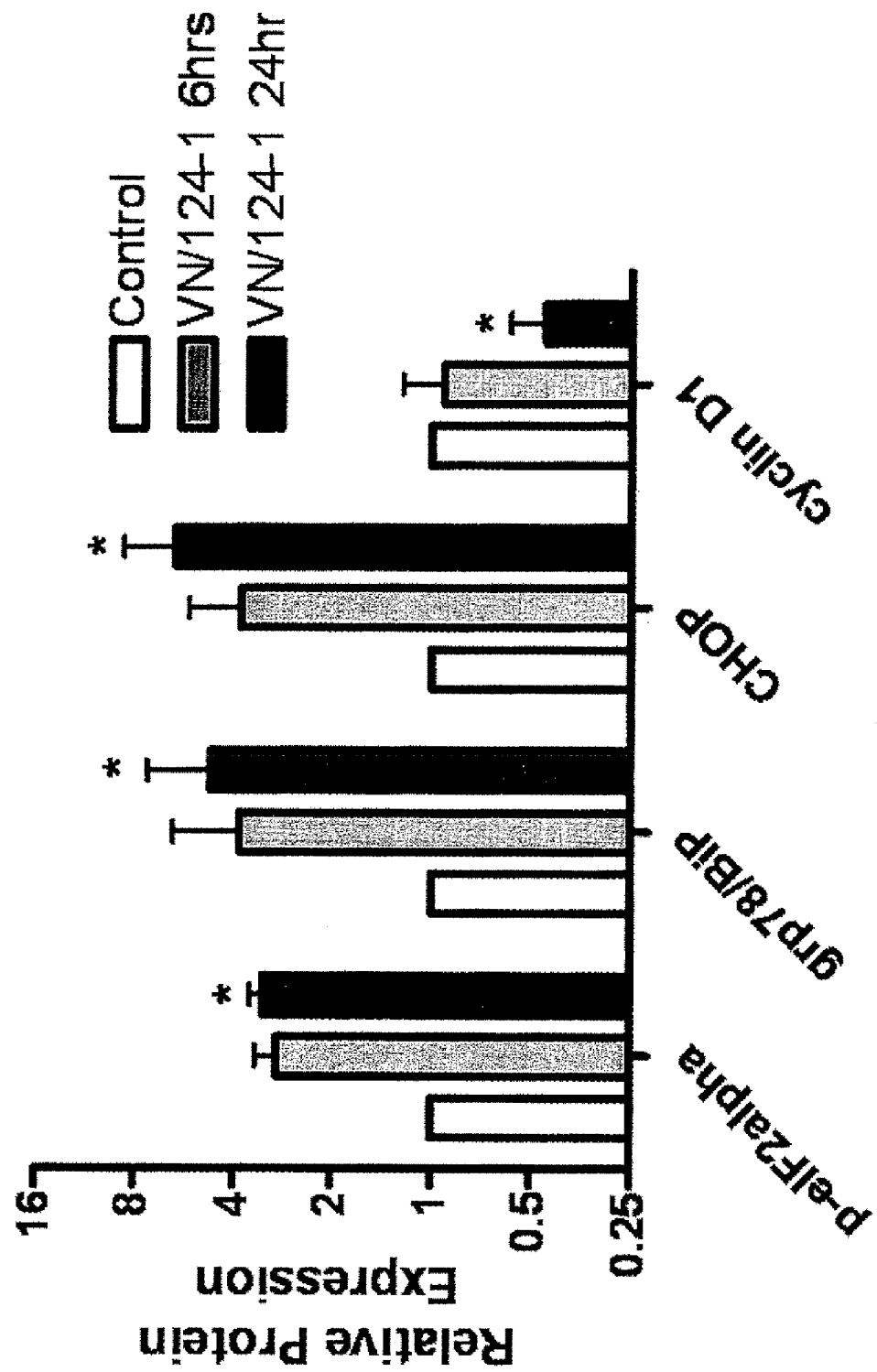
FIG. 7 depicts the densitometry quantitation of western blot results. Expression is measured as fold change relative to control.

As shown in FIGS. 5 and 7, 20 μM VN/124-1 induced the phosphorylation of eIF2α at 6 and 24 hrs. The drug also significantly induced the expression of the molecular chaperone gp78/BiP, a well established marker of ER-stress. The up-regulation of CHOP was also confirmed at the protein level. As mentioned previously, phosphorylation of eIF2α is known to attenuate translation of many transcripts including cyclin D1, and the results herein confirm the down-regulation of cyclin D1 protein significantly after 24 hrs. As discussed above, VN/124-1 had no effect on cyclin D1 mRNA levels, suggesting this down-regulation is indeed occurring at the translational level. Taken together these findings strongly support the hypothesis that VN/124-1 induces the ERSR.

Cell Cycle Analysis Results

Figure 8:
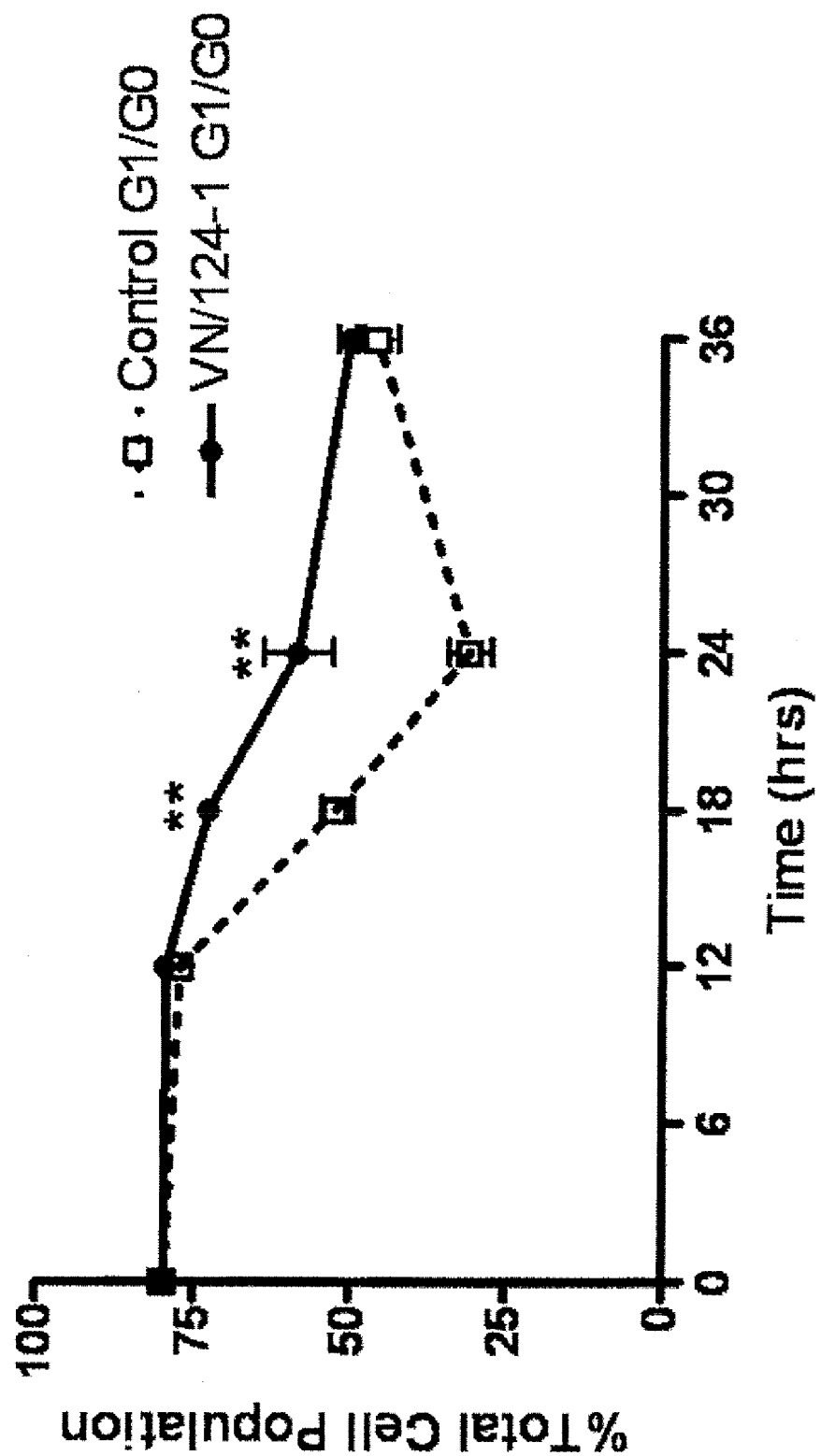
FIG. 8 depicts the effect of 20 μM VN/124-1 cell cycle progression. PC-3 cells were synchronized in G1/G0 by serum starvation for 96 hrs. Cells were then incubated with full growth medium containing either vehicle or 20 μM VN/124-1, and cell cycle was assessed at relative timepoints by flow cytometry. All graphs represent the mean±SEM of 3 independent experiments. *p<0.05, p<0.01, *p<0.001.

Treatment with 20 μM VN/124-1 prevented the exit from G1 phase of the cell cycle in synchronized cells (FIG. 8), which resulted in a significant increase in the amount of cells in G1/G0 at 18 and 24 hrs. These data are consistent with the loss of cyclin D1 protein expression and subsequently cyclin E2 transcription, as both are needed for transition to the S-phase of the cell cycle. These data are also in accord with the microarray data herein showing VN/124-1 down-regulates genes involved in DNA replication.

$Ca^{2+}$ Analysis Results

Figure 9A:
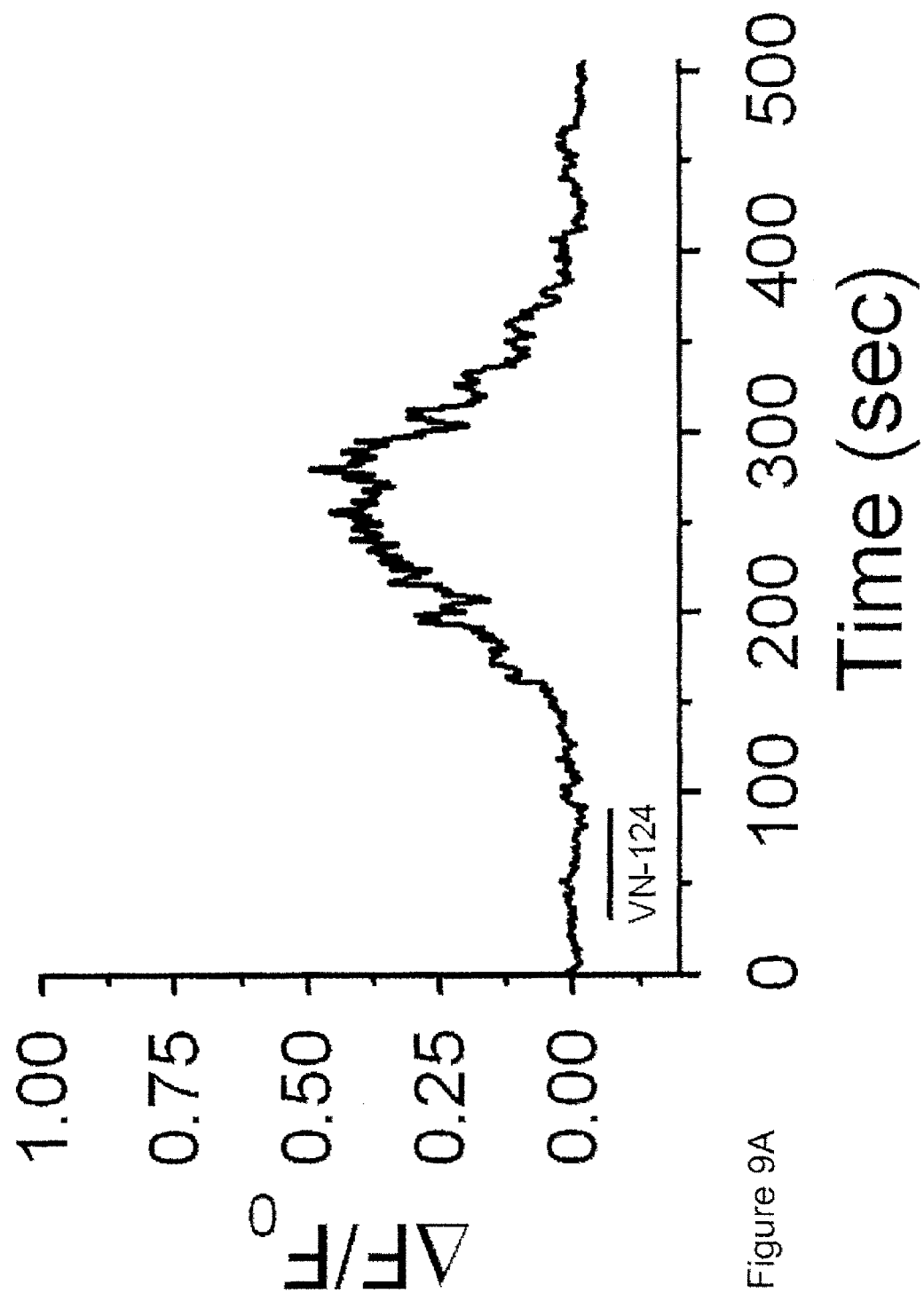
FIG. 9 depicts VN/124-1 inducing release of calcium from the ER. PC-3 cells loaded with Fluo-3AM were treated with 20 μM VN/124-1 in the presence (A) or absence (B) of extracellular calcium. Mean peak values are 0.613 and 0.967, respectively. For all treatments, $Ca^{2+}$ transients were measured in individual cells (n=9, 12, 9, respectively) as described herein.
Figure 9B:
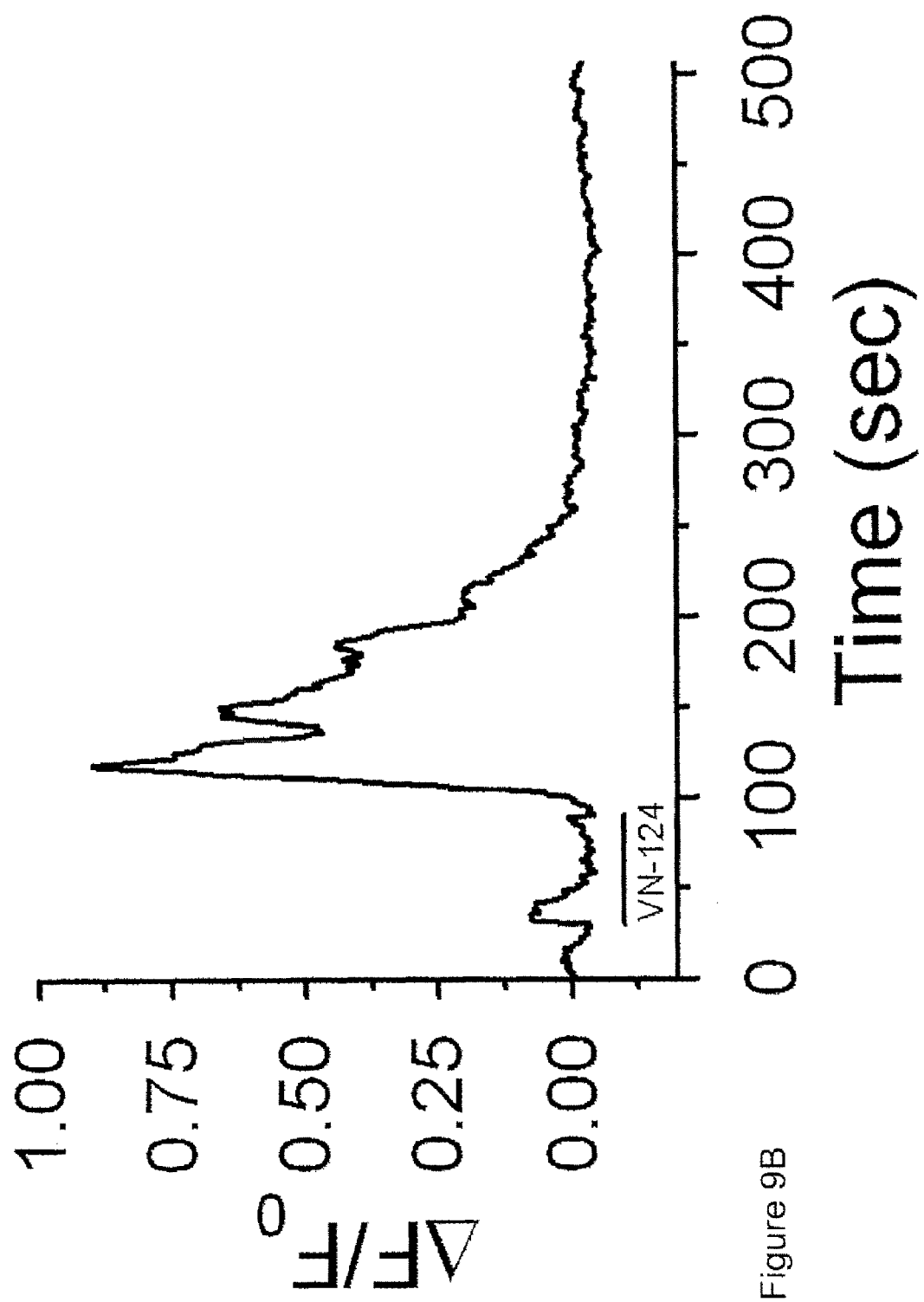
Figure 11:
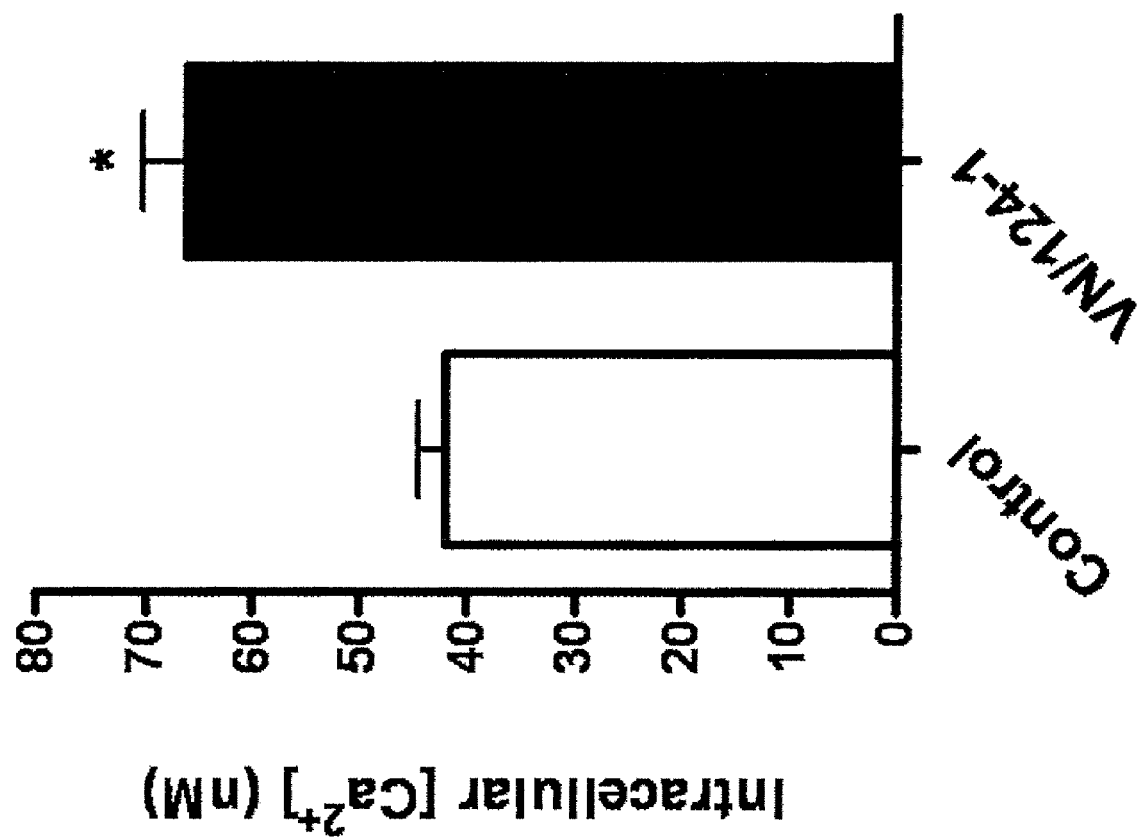
FIG. 11 depicts absolute $[Ca^{2+}]_i$ being measured in cells that were dosed with 20 μM of VN/124-1 or vehicle for 24 hrs. Cells were dosed and then loaded with Fura-2AM. Individual cells were counted (n=30, and 29 for Control and VN/124-1, respectively). *p<0.05

To determine if VN/124-1 induces the—PC-3 cells were treated with 20 μM VN/124-1 and measured relative changes in intracellular calcium concentrations $[Ca^{2+}]_i$ using the calcium sensitive fluorescent dye, Fluo-3AM. As seen in FIG. 9A, VN/124-1 induced an immediate transient rise in $[Ca^{2+}]_i$ (mean ΔF/Fo0.613). This transient rise in $[Ca^{2+}]_i$ was not reduced when extracellular calcium was removed from the bath (mean ΔF/Fo=0.967; FIG. 9B), but was completely abolished when ER calcium stores were depleted by pretreatment with the sarco/endoplasmic reticulum $Ca^{2+}$-ATPase (SERCA) inhibitor cyclopiazonic acid (CPA) (FIG. 10). Finally, the sustained effect of VN/124-1 was measured on absolute $[Ca^{2+}]_i$ using Fura-2AM. Treatment of PC-3 cells for 24 hrs with 20 μM of VN/124-1 resulted in a significant rise in $[Ca^{2+}]_i$ from a mean of about 42.05 nM in control cells to about 66.21 nM in VN/124-1 treated cells (FIG. 11). These results clearly demonstrate that VN/124-1 is capable of inducing $Ca^{2+}$ release from ER-stores, resulting in a sustained rise in $[Ca^{2+}]_i$.

Co-Administration of VN/124-1 with a Known ERSR Inducer

Figure 12:
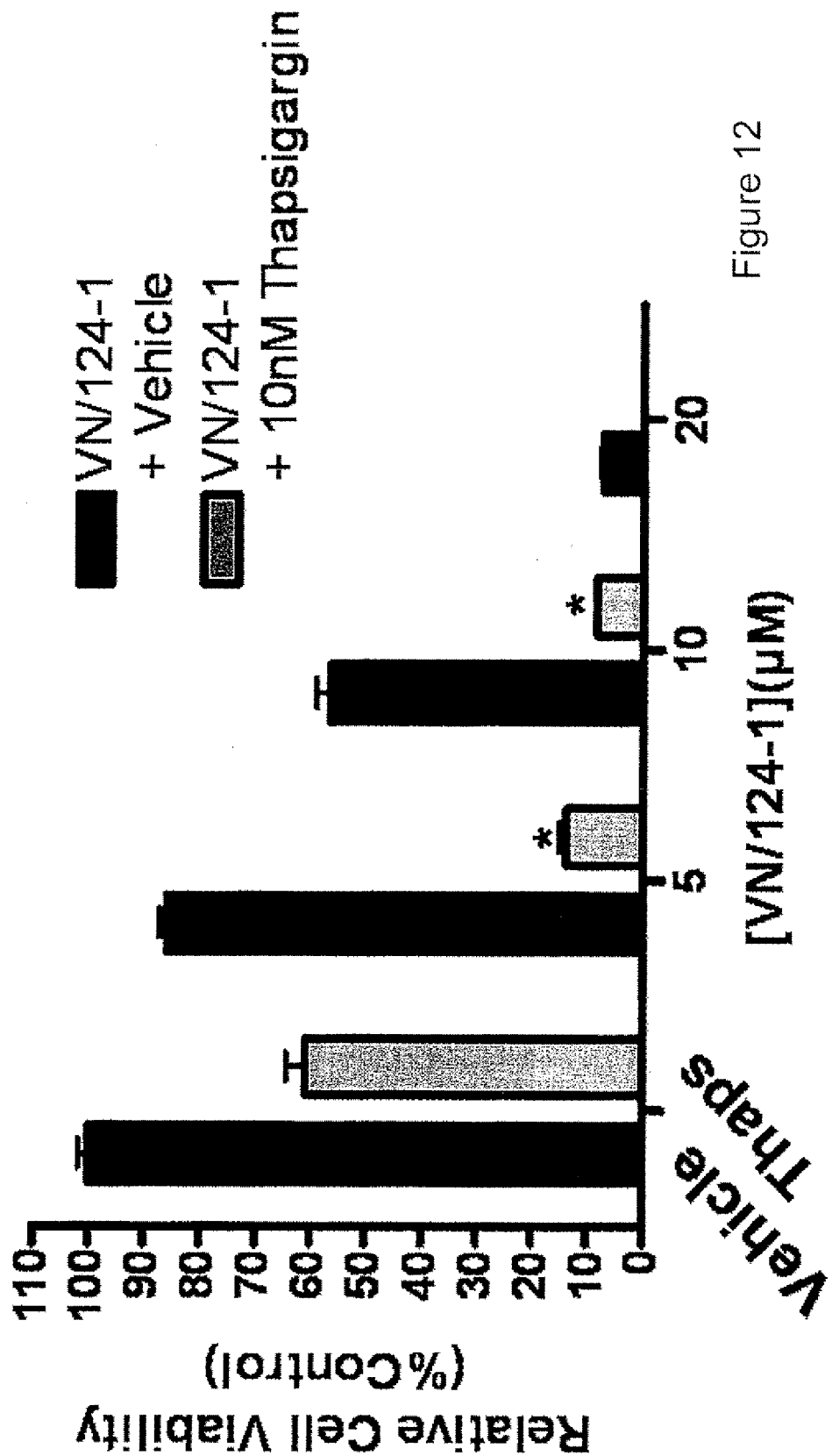
FIG. 12 depicts the results of co-administration of VN/124-1 and thapsigargin. PC-3 cells were treated with 5, 10, or 20 μM VN/124-1 plus 10 nM thapsigargin or vehicle (DMSO) for 96 hrs and cell viability was assessed via MTT assay. The combination was synergistic in inhibiting PC-3 cell growth at all three (CI=0.40, 0.58, 0.77, respectively). *p<0.01. (B)
Figure 13:
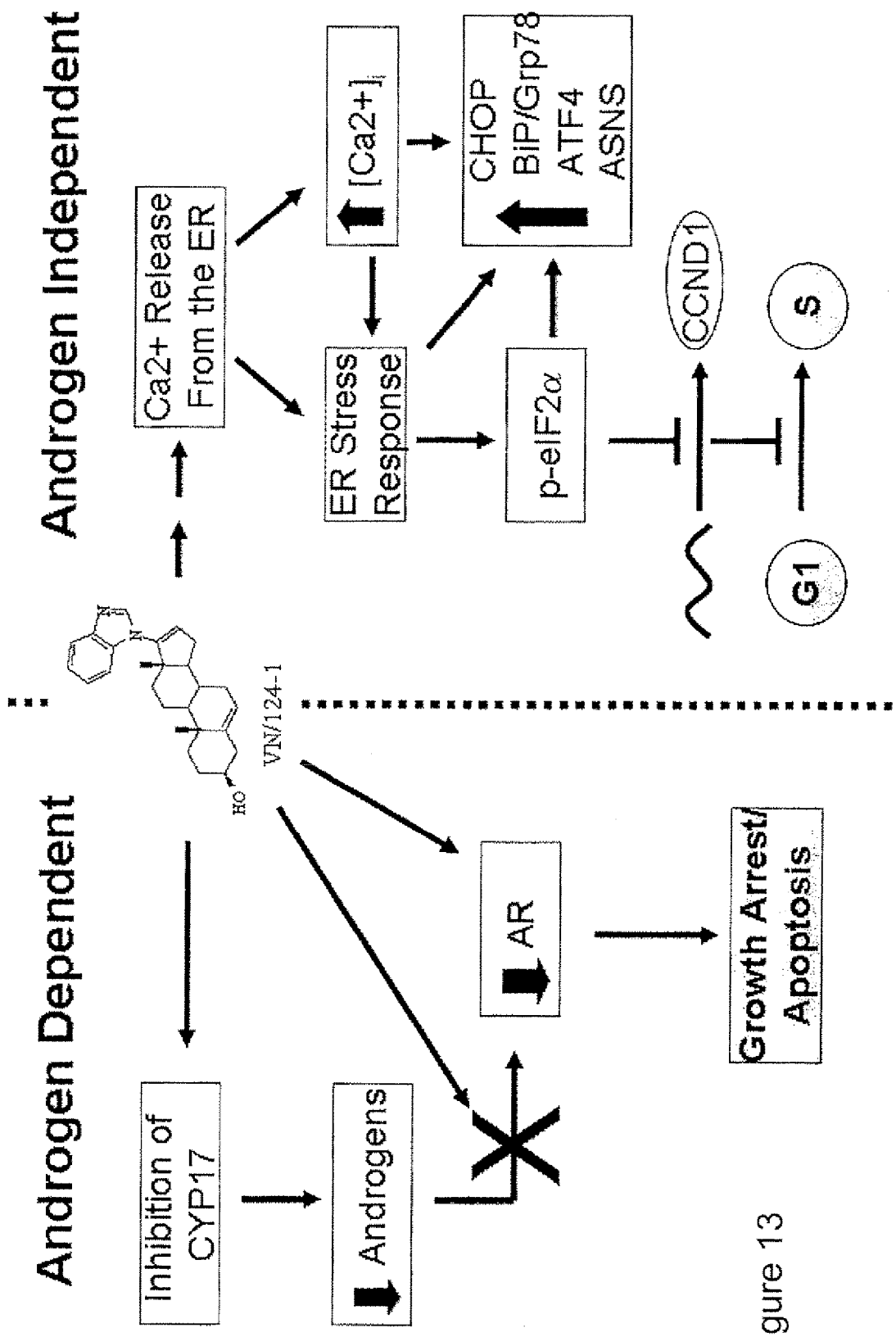
FIG. 13 depicts various schemes of VN/124-1's androgen-dependent and independent mechanisms of action.

To determine if VN/124-1 would act synergistically with a compound known to induce ER stress, PC-3 cells were treated with VN/124-1 and the SERCA pump inhibitor, thapsigargin. A sub-toxic dose of 10 nM thapsigargin was combined with 5, 10, and 20 μM of VN/124-1 and cell viability was measured after 96 hrs. As shown in FIG. 12, thapsigargin and VN/124-1 acted synergistically to inhibit the growth of PC-3 cells at all three concentrations (CI=0.40, 0.58, 0.77, respectively), further implicating the ERSR and calcium disruptions as VN/124-1's mechanism of action.

What is claimed is:

1. A method of causing an effect in a prostate cancer cell, wherein the effect is selected from the group consisting of inducing cell cycle arrest in a cell, inducing growth arrest in a cell and inducing apoptosis in a cell, the method comprising coadministering, sequentially or coextensively, to the prostate cancer cell of a patient in need thereof an effective dose of a combination of an amount of a compound of Formula II and

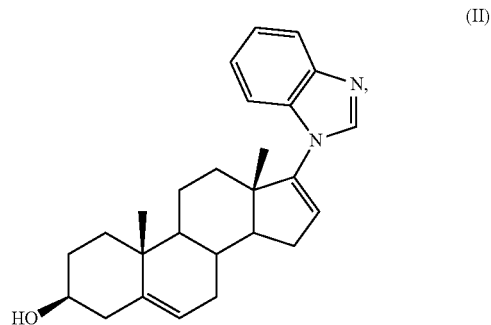 [SMILES: C[C@]12CC[C@H](O)CC1=CCC1C2CC[C@]2(C)C(n3cnc4ccccc43)=CCC12]

(II)

and an amount of thapsigargin, wherein coadministration of the amount of the compound and the amount of thapsigargin to the cell causes said effect in the cell.

2. The method of claim 1, wherein the cell is a human cell.

3. The method of claim 1, wherein the effect is inducing apoptosis.

4. The method of claim 1, wherein the effect is inducing cell cycle arrest.

5. The method of claim 1, wherein the effect is cell growth arrest.

6. The method of claim 1, wherein the amount of thapsigargin is 10 nM thapsigargin.

7. The method of claim 1, wherein the amount of the compound of Formula II is between about 5 μM to 10 μM.

8. The method of claim 1, wherein the coadministering further comprises administering an amount of an additional agent that induces ER stress, wherein the additional agent that induces ER stress is selected from the group consisting of cisplatin, gentamicin, bortezomib, eeyarestatin, sorafenib, and docosahexaenoic acid (DHA).

* * * * *

UNITED STATES PATENT AND TRADEMARK OFFICE
CERTIFICATE OF CORRECTION

PATENT NO. : 8,785,423 B2
APPLICATION NO. : 12/937900
DATED : July 22, 2014
INVENTOR(S) : Vincent Njar et al.

It is certified that error appears in the above-identified patent and that said Letters Patent is hereby corrected as shown below:

IN THE SPECIFICATION:

In column 1, lines 18-22, please replace "Part of the work performed during development of this invention utilized U.S. Government funds under National Institutes of Health Grant Numbers CA117991, CA027440 and ES007263. The U.S. Government has certain rights in this invention." with -- This invention was made with government support under Grant Numbers CA117991, CA027440, and ES007263 awarded by the National Institutes of Health. The government has certain rights in the invention. --.

Signed and Sealed this
Sixth Day of January, 2015

Michelle K. Lee
*Deputy Director of the United States Patent and Trademark Office*